(12) United States Patent
Hahn et al.

(10) Patent No.: US 8,470,998 B2
(45) Date of Patent: Jun. 25, 2013

(54) POSITIVE CONTROLS FOR EXPRESSION MODULATING EXPERIMENTS

(75) Inventors: Peter Hahn, Bergisch Gladbach (DE); Jörg Dennig, Langenfeld (DE); Wolfgang Bielke, Köln (DE); Jie Kang, Mettmann (DE)

(73) Assignee: Qiagen GmbH, Hilden (DE)

( * ) Notice: Subject to any disclaimer, the term of this patent is extended or adjusted under 35 U.S.C. 154(b) by 33 days.

(21) Appl. No.: 12/809,523

(22) PCT Filed: Dec. 29, 2008

(86) PCT No.: PCT/EP2008/011130
§ 371 (c)(1),
(2), (4) Date: Oct. 21, 2010

(87) PCT Pub. No.: WO2009/083253
PCT Pub. Date: Jul. 9, 2009

(65) Prior Publication Data
US 2011/0034535 A1 Feb. 10, 2011

(30) Foreign Application Priority Data
Dec. 28, 2007 (EP) .................... 07025198

(51) Int. Cl.
*C07H 21/00* (2006.01)
*C07H 21/02* (2006.01)
*C12N 15/00* (2006.01)
*A01N 43/04* (2006.01)

(52) U.S. Cl.
USPC .......... 536/24.5; 536/23.1; 435/6.1; 435/455; 514/55; 424/93.2

(58) Field of Classification Search
None
See application file for complete search history.

(56) References Cited

U.S. PATENT DOCUMENTS 7,598,370 B2 10/2009 Khvorova et al.

2007/0031844 A1 2/2007 Khvorova et al.
2010/0273856 A1* 10/2010 Smith et al. ............... 514/44 A
2010/0285484 A1 11/2010 Lader

FOREIGN PATENT DOCUMENTS

WO WO 03/070283 A2 8/2003
WO WO 2006/060246 A2 6/2006

OTHER PUBLICATIONS

Andersen et al., "Comparison of Gene Silencing in Human Vascular Cells Using Small Interfering RNAs," *J Am Coll Surg 204*(3): 399-408, Mar. 2007.
Anonymous [online], "Customer Information: Here is how we can help you get results," Dec. 2, 2007, XP002522531, retrieved from the Internet: URL:http://www.rnax.de.downloads/RNAx%20Customer%20Info%20December%202007.pdf> [retrieved on Apr. 3, 2009].
Lei et al., "siRNA-Mediated *BCL-2* and *BCL-XL* Gene Silencing Sensitizes Human Hepatoblastoma Cells to Chemotherapeutic Drugs," *Clinical and Experimental Pharmacology and Physiology 34*: 450-456, 2007.
Liu et al., "Normal Cells, but Not Cancer Cells, Survive Severe Plk1 Depletion," *Molecular and Cellular Biology 26*(6): 2093-2108, Mar. 2006.
Reagan-Shaw et al., "Silencing of polo-like kinase (P1k) 1 via siRNA causes induction of apoptosis and impairment of mitosis machinery in human prostate cancer cells: implications for the treatment of prostate cancer," *The FASEB Journal 19*: 611-613, Apr. 2005.
Wang et al., "Development and validation of vectors containing multiple siRNA expression cassettes for maximizing the efficiency of gene silencing," *BMC Biotechnology 6*: 50 (7pages), Dec. 22, 2006.

* cited by examiner

*Primary Examiner* — Jennifer Pitrak McDonald
(74) *Attorney, Agent, or Firm* — SEED IP Law Group PLLC

(57) ABSTRACT

The invention pertains to the use of an apoptosis inducing combination of at least a. a first expression modulating compound silencing the expression of at least a first target gene involved in apoptosis and b. a second expression modulating compound silencing the expression of at least a second target gene involved in apoptosis as a positive control in expression modulating assays. Also provided are suitable methods, kits and compositions.

14 Claims, 15 Drawing Sheets

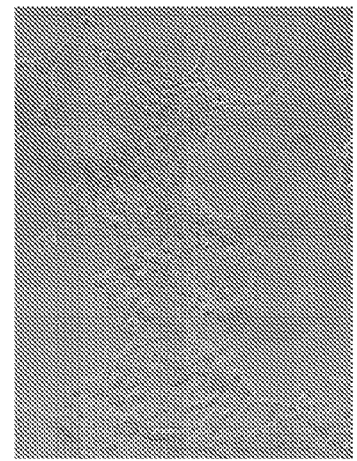
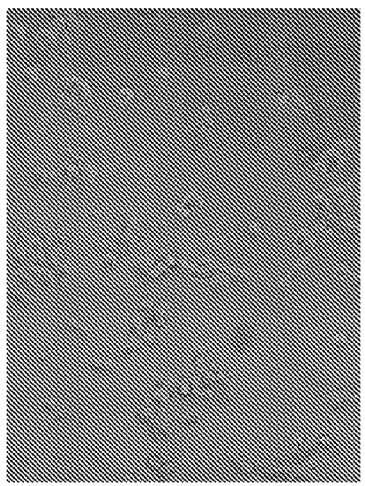
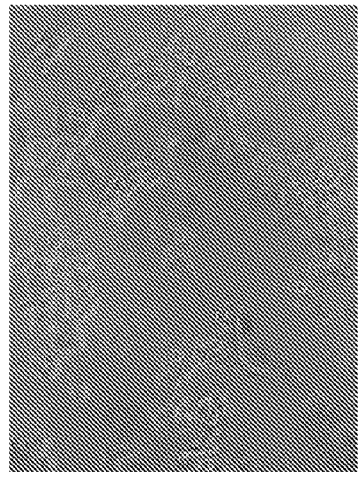
Fig. 3A

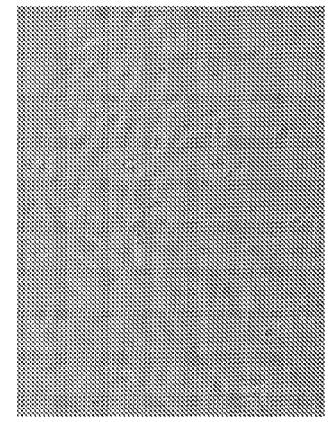
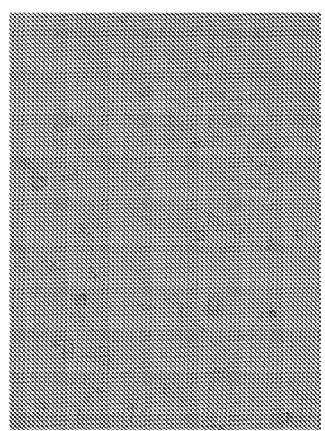
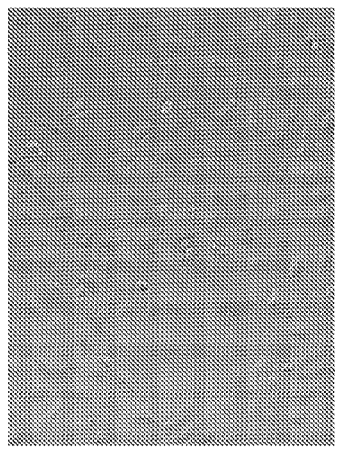
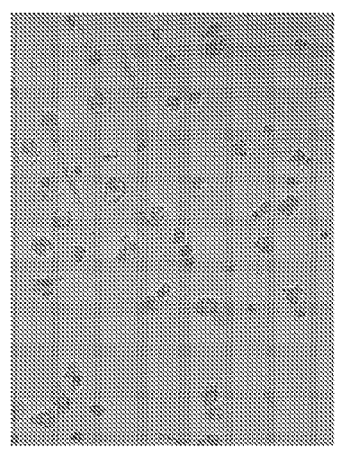
Fig. 3D

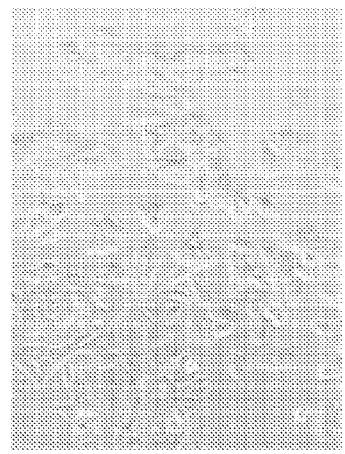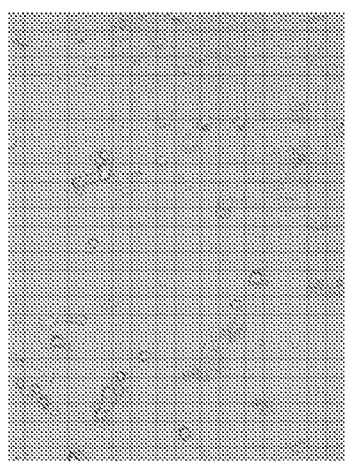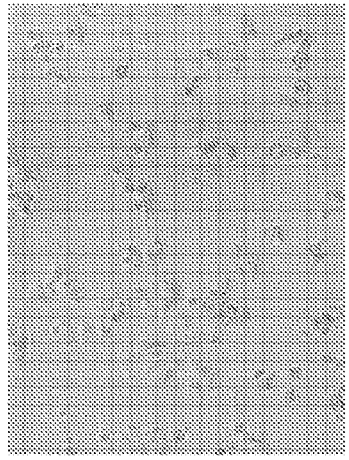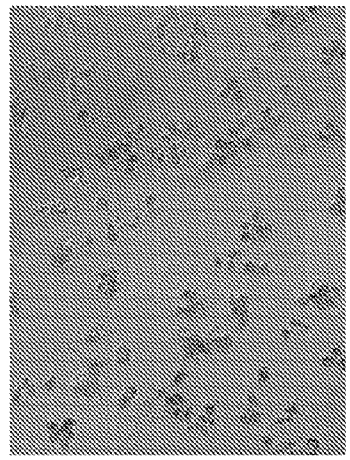
*Fig. 3F*

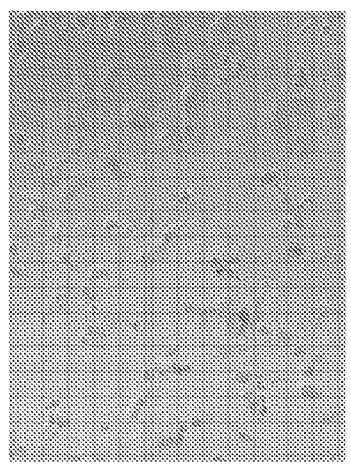 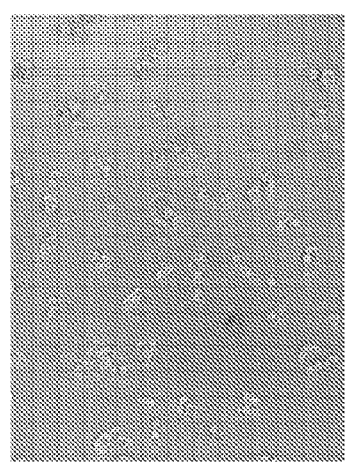
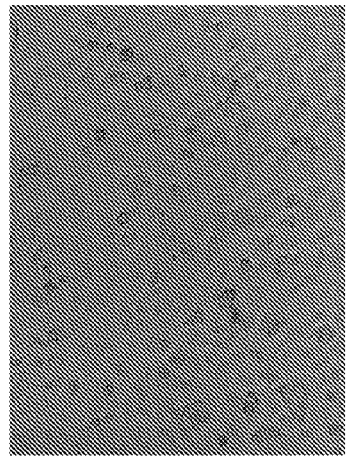 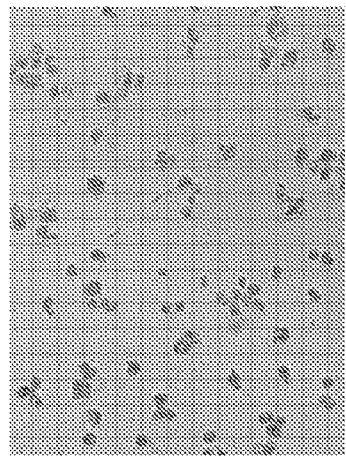
Fig. 3G

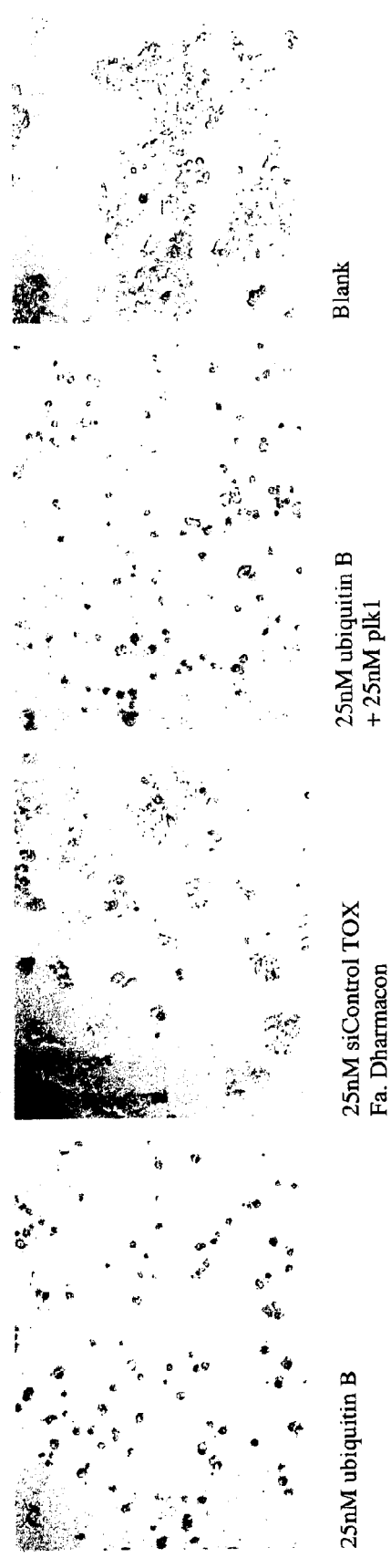
Fig. 5. – continued
HepG2

POSITIVE CONTROLS FOR EXPRESSION MODULATING EXPERIMENTS

STATEMENT REGARDING SEQUENCE LISTING

The Sequence Listing associated with this application is provided in text format in lieu of a paper copy, and is hereby incorporated by reference into the specification. The name of the text file containing the Sequence Listing is 771025_401USPC_SEQUENCE_LISTING.txt. The text file is 7 KB, and was created and submitted electronically via EFS-Web on Jun. 18, 2010.

The present invention pertains to the use of certain expression modulating compounds as positive controls in assay systems as well as to the respective expression modulating compounds.

Many methods are known in the state of the art that target and/or influence gene expression. Earlier methods modified the DNA, e.g. by mutation or recombination. Such methods, however, altered the genetic identity of the organism.

Several new techniques were established in the last years that did not target the DNA but the RNA (mRNA) in order to alter/modulate gene expression. These RNA-targeting techniques allow modulation of gene expression such that only minimal levels of functional mRNA remain, thereby allowing even the regulation of essential genes. These techniques allow the creation of specific phenotypes as well as the analysis of the gene function in different developmental stages.

One of the earlier methods of these RNA—targeting techniques to modulate, in particular down-regulate gene expression was the antisense technology. Antisense polynucleotides are designed to specifically bind to RNA, resulting in the formation of RNADNA or RNA-RNA hybrids, with an arrest of reverse transcription or messenger RNA translation. Antisense polynucleotides based on a selected sequence can thus modulate the expression of the corresponding gene as the mRNA is targeted and e.g. translation of the mRNA is at least partially inhibited. Many forms of antisense have been developed and can be broadly categorized into enzyme-dependent antisense or steric blocking antisense. Enzyme-dependent antisense includes forms dependent on RNase H activity to degrade target mRNA, including single-stranded DNA, RNA, and phosphorothioate antisense.

Antisense polynucleotides are typically generated within the cell by expression from antisense constructs that contain the antisense strand as the transcribed strand. Antisense polynucleotides will bind and/or interfere with the translation of the corresponding mRNA. As such, antisense may be used for research purposes as well as therapeutically e.g. to inhibit the expression of oncogenes.

Antisense RNA or antisense oligodeoxynucleotides (antisense ODNs) can both be used and may also be prepared in vitro synthetically or by means of recombinant DNA techniques. Both methods are well within the reach of the person skilled in the art. ODNs are smaller than complete antisense RNAs and have therefore the advantage that they can more easily enter the target cell. In order to avoid their digestion by DNAse, ODNs and antisense RNAs may be chemically modified.

Trans-cleaving catalytic RNAs (ribozymes) are RNA molecules possessing endoribonuclease activity. Ribozymes are specifically designed for a particular target, and the target message must contain a specific nucleotide sequence. They are also established expression modulators. They are engineered to cleave any RNA species sitespecifically in the background of cellular RNA. The cleavage event renders the mRNA unstable and prevents protein expression. Importantly, ribozymes can be used to inhibit expression of a gene of unknown function for the purpose of determining its function in an in vitro or in vivo context, by detecting the phenotypic effect.

A further mechanism for modulating expression on a post-transcriptional level is RNA interference (RNAi) which is a mechanism for RNA guided regulation of gene expression in which double-stranded ribonucleic acid molecules inhibit the expression of genes with complementary nucleotide sequences. Conserved in most eukaryotic organisms, the RNAi pathway is thought to have evolved as form of innate immunity against viruses and also plays a major role in regulating development and genome maintenance.

The RNAi pathway is initiated by the enzyme dicer, which cleaves double-stranded RNA (dsRNA) to short double-stranded fragments of usually approximately 20 to 25 basepairs. One of the two strands of each fragment, known as the guide strand, is then incorporated into the RNA induced silencing complex (RISC) and base-pairs with complementary sequences. The most well-studied outcome of this recognition event is a form of post-transcriptional gene silencing. This occurs when the guide strand base-pairs with the messenger RNA (mRNA) molecule and induces degradation of the mRNA by argonaut, the catalytic component of the RISC complex. The short RNA fragments are known as small interfering RNA (siRNA) when they derive from exogenous sources and microRNA (miRNA) when they are produced from RNA coding genes in the cells' own genome.

The selective and robust effect of RNAi on gene expression makes it a valuable research tool, both in cell culture and in living organisms. Synthetic dsRNA introduced into cells can induce suppression of specific genes of interest. The effect of these genes on the phenotype of the cells can then be analyzed by studying the effect of the gene silencing. RNAi may also be used for large-scale screens that systematically shut down each gene in the cell, which can help identify the components necessary for a particular cellular process or an event such as for example, cell division.

Due to its advantages siRNA-mediated RNAi has become an indispensable tool in functional genomic research. Chemically synthesized siRNA reagents that target every gene in a human, mouse and rat genome are available for convenient delivery in vitro. Data acquired from RNAi experiments are used to support important conclusions about how genes function.

In addition to their role in the RNAi pathway, siRNAs also act in RNAi related pathways, for example as an antiviral mechanism or in shaping the chromatin structure of a genome; the complexity of these pathways is only now being elucidated.

For the above reasons, the RNA interference pathway is often exploited in experimental biology to study the function of genes in cell culture and in vivo in model organisms. Double-stranded RNA is synthesized with a sequence complementary to a target sequence of a gene of interest, usually a 18 to 30 mer and introduced into the cell or organism, where it is recognized as exogenous genetic material and activates the RNAi pathway. Using this mechanism, researchers can cause a drastic decrease in the expression of the targeted gene. Studying the effects of this decrease can show the physiological role of the respective targeted gene product. Since RNAi may not necessarily totally abolish expression of the gene, this technique is sometimes referred to as a "knockdown" to distinguish it from "knockout" procedures in which expression of a gene is entirely eliminated e.g. by introducing a knock-out mutation in the target gene.

Depending on the organism and the experimental system, the exogenous RNA may be a long strand designed to be cleaved by dicer or short RNAs designed to serve as siRNA substrates. In most mammalian cells, shorter RNAs are used because long double-stranded RNA molecules induce the mammalian interferon response, a form of innate immunity that reacts non-specifically to foreign genetic material.

These molecules are usually introduced in the cells by appropriate transfection methods.

Specialized laboratory techniques have also been developed to improve the utility of RNAi in mammalian systems by avoiding the direct introduction of siRNA, for example, by stable transfection with a plasmid encoding the appropriate sequence from which siRNA can be transcribed, or by more elaborate lentiviral vector systems allowing the inducible activation or deactivation of transcription, known as conditional RNAi.

In order to ensure that the conclusion drawn from any expression modulating experiment such as e.g. an antisense or a RNAi experiment are accurate, it is important to include proper controls in every expression modulating experiment. Such controls strengthen the drawn conclusions and ensure that the performed expression modulating experiments result in the expected silencing. Appropriate experimental controls are thus of utmost importance in order to maximize the value of the generated data.

Commonly, at least three types of control samples are run e.g. in every RNAi experiment: a positive control, a negative control and an untreated control. Positive controls may monitor efficiency of e.g. siRNA delivery into cells (transfection efficiency) or may monitor the proper function of an assay and negative controls distinguish sequencespecific silencing from non-specific effects. Untreated samples determine the baseline level of cell viability, the cell phenotype and the target gene level.

In order to achieve successful gene silencing, efficient delivery of the expression modulating compound such as an siRNA into the cells of interest is important. E.g. siRNA delivery efficiency can vary between individual cell types used and the delivery method used.

In RNAi experiments, as positive controls usually siRNA are used that target a housekeeping gene. Popular target genes are for example GAPDH, lamin, MAPK1, beta-actin, p53, cyclophilin B and luciferase GL2. The positive controls as are presently often aimed at in the state of the art target a house keeping gene that this constitutively and abundantly expressed in a wide variety of cell types.

Many positive controls demand elaborate and time-consuming testing methods. Many researchers are currently using quantitative RT-PCR or western blotting to assess the compound induced knockdowns. While accurate, these techniques can be very time-consuming and labor intensive. Another means to monitor expression modulating compound/siRNA delivery is the use of fluorescently labeled compounds/siRNAs. This method has the advantage of speed, but it can be unreliable since the compounds/siRNA can be trapped in endosomes or other subcellular compartments that keep the expression modulating compound such as a siRNA from targeting their target mRNA.

Functionally validated siRNAs can be used as positive controls. Gene silencing mediated by them is usually determined either on the mRNA or on the protein level. These analyses, however, are very elaborate and time-consuming. This has the effect that at the time, when one wants to interpret e.g. HTS experiments, one does not have the information regarding the gene silencing effect obtained with the positive controls. Therefore, one has to perform part of the experiments and interpretation without the information regarding their comparability. This has the effect that sometimes one must discard portions of the already obtained primary data (for example when the transfection did not function efficiently).

As outlined above, also fluorescence labeled siRNAs are used in order to control the transfection rate. However, due to the low amount of fluorescence of the individual labeled siRNA molecules, rather high siRNA concentrations need to be used for a secure detection of the signals as this would be necessary for biologically active siRNAs. This further complicates the comparability of the respective transfection assays and makes fluorescence labeled siRNAs unsuitable for reliable HTS approaches.

Gene silencing effects which are caused by siRNA transfection in eukaryotic cells always have a transient character. If one wants to perform RNAi experiments with siRNAs in a high-through-put screening assay (HTS) one must prepare the whole series of experiments on a plurality of e.g. microtiter plates in multiple replicas. Due to many factors which influence the transfection efficiency of the used cellular systems (for example the kind of cells, charge fluctuations of the used transfection reagents and the like) it is not always easy to compare experiments, that were done on different days or to compare gene silencing effects which were done with different culture plates.

For this purpose, a validated positive control siRNA, which is run on each individual plate and in each experiment, would be helpful that can be used in order to normalize the measured gene silencing effect. As most HTS experiments are interpreted by phenotypic analysis methods, a positive control, wherein the successful transfection leads to a clear, easy to identify phenotype, would be a valuable tool for the respective user.

A phenotype which is rather easy to determine via microscopic techniques is apoptosis and thus cell death. In particular in the case of adherent cells, dying (apoptotic or necrotic) cells changes their morphology in a very characteristic way, as they round up and detach from the dish plate they adhered to. Therefore, the silencing of genes with siRNAs which induce apoptosis in the cell is a promising possibility to develop a phenotypic control siRNAs.

For example Dharmacon has developed a toxic siRNA, which may induce cell death as a phenotypic detectable effect. However, scientific publications show that this siRNA does not induce a detectable cell death e.g. in HEK 293 cells (Reinolds et al, 2006). Further experiments also showed that this toxic siRNA can also not induce cell death in A 549, Huh7 and HepG2 cells. The applicability is thus limited.

There is thus a strong need for a siRNA or a siRNA composition, which induces phenotypically detectable apoptosis in many cell lines and primary cell preparations which can thus be used as a reliable phenotypic control.

It is the object of the present invention to provide a positive control for use an expression modulating experiments, in particular RNAi experiments which is effective and convenient to analyze.

This object is solved by using a combination of at least a) a first expression modulating compound silencing the expression of a first target gene involved in apoptosis and b) a second expression modulating compound silencing the expression of a second target gene involved in apoptosis.

By using a respective combination of the first and second expression modulating compounds silencing different target genes involved in apoptosis, apoptosis is efficiently induced in the cells transfected with the respective combination of said first and second expression modulating compound.

Therefore, the combination of said first and second expression modulating compound efficiently induces an apoptotic phenotype in the transfected cells.

A target gene involved in apoptosis means a gene wherein silencing either directly or indirectly induces or promotes apoptosis. Therefore, the expression of genes can be targeted which are either directly involved in apoptosis or which are involved in essential processes of the cell so that their downregulation induces, results in or promotes apoptosis. For the teachings of the present invention it is decisive that the combination of said at least the first and second expression modulating compound induces an apoptotic phenotype in the transfected cells.

Commonly, the term "gene" particularly refers to a section of the DNA, which encodes the information for the production of a biologically active RNA. Said biologically active RNA is obtained through transcription. Many different types of biologically active RNA can be generated from a gene. The most common RNA transcribed from a gene is mRNA, which is translated into a protein. In eukaryotes, genes usually show an intron/exon structure. However, the transcription of a gene may also result in non-coding RNA. A non-coding RNA (ncRNA) is a functional RNA molecule that is not translated into a protein. The DNA sequence from which a non-coding RNA is transcribed as the end product is usually referred to as an RNA gene or non-coding RNA gene. Therefore, the term "gene" includes genes encoding proteins as well as genes leading to the generation of non-coding RNA. However, preferably, the term "gene" refers to genes encoding a polypeptide, such as a protein.

Preferred target genes are Plk1 and ubiquitin, as is described in detail below. The downregulation of each of said genes alone does not necessarily result in a visible apoptotic phenotype. However, by using a combination of said expression modulating compounds, a visible apoptotic phenotype is obtained rather quickly. Therefore, the ubiquitin and the Plk1 gene are preferred examples of genes involved in apoptosis as defined in accordance with the present invention.

Preferred non-coding RNA elements that can be targeted by the first, the second and/or a further expression modulating compound are repetitive elements such as LINEs (long interspersed nuclear elements) and SINEs (short interspersed nuclear elements), in particular Alu and B1 repetitive elements. These repetitive elements are often found in the untranslated regions of protein-coding transcripts, usually in the 3' UTR even though they may also be present in the 5' UTR. By targeting the respective repetitive elements, usually several gene transcripts (comprising the targeted repetitive elements) are silenced, thereby severely disturbing the cell function which in turn leads to apoptosis. Respective embodiments are also encompassed by the teachings of the present invention. As is shown below, the combination of an expression modulating compound downregulating the expression of a B1 repetitive element with an expression modulating compound downregulating the expression of ubiquitin, in particular ubiquitin B, leads to a visible apoptotic phenotype in the transfected cells. Therefore, genes comprising SINE elements, and in particular B1 repetitive elements are examples of genes involved in apoptosis as defined in accordance with the present invention. Targeting the respective elements in the corresponding transcripts by the expression modulating compounds of the present invention efficiently silences the corresponding genes, thereby severely disturbing the cell function, which leads to apoptosis.

As is outlined above, apoptosis leads to phenotypic changes in the cells, which can for example be detected by using a microscope. Thereby, an efficient positive control is provided for use in an expression modulating assay, which is easy to determine based on the phenotype of the presented cells. Thereby, an easy and quick positive control which can be analyzed based on the phenotype of the cells is provided.

Because regular laboratory equipment such as a microscope can be used for analyzing the positive control provided by the present invention, the analysis of the positive control according to the present invention can be performed very easily using established systems.

The first and second expression modulating compounds can be transfected into the cells either at the same time, for example by using a transfection composition comprising both expression modulating compounds or by sequentially introducing the expression modulating compounds into the cells. It is also within the scope of the present invention to use further expression modulating compounds which silence further target genes involved in apoptosis or leading to apoptosis. Many embodiments are feasible. Accordingly, for fulfilling the principle of the present invention it is only decisive that the first and the second expression modulating compound are introduced into the cells in order to provide efficient gene silencing of the target genes, thereby inducing an apoptotic phenotype and hence an effective positive control which can be used to determine transfection efficiency.

The use of at least two expression modulating compounds such as RNAi compounds (preferably siRNAs) silencing the expression of two different target genes involved in apoptosis has the advantageous effect that apoptosis is induced very efficiently and therefore is also detectable within a rather short time frame. As is shown in the experimental section, the transfection with two siRNAs targeting different target genes involved in apoptosis results in a synergistic effect which is visible and therefore analyzable already as early as 72 or even 48 hours after transfection. This is not achieved when using only one siRNA targeting one target gene involved in apoptosis. Of course, it is not necessary that all cells undergo apoptosis when contacted with the combination according to the present invention. However, when transfection is performed correctly, apoptosis should be induced to a visible degree within a given time frame of several hours to days.

The first and/or the second target gene can be selected from the group consisting of Plk1, ubiquitin, preferably ubiquitin B, and genes comprising repetitive elements, such as SINE elements, in particular Alu elements and B1 repetitive elements.

According to one embodiment, the first target gene involved in apoptosis which is targeted by the first expression modulating compound is Plk1 (polokinase 1). Plk1 is an enzyme that catalyzes the chemical reaction of ATP and a protein to ADP+a phosphoprotein. Thus, the two substrates of this enzyme are ATP and a protein, whereas its two products are ADP and phosphoprotein. This enzyme belongs to the family of transferases, specifically those transferring a phosphate group to the sidechain oxygen atom of serine or threonine residues in proteins (protein-serine/threonine kinases). This enzyme participates in particular in several metabolic pathways, thereunder the cell cycle.

Preferably, the second target gene involved in apoptosis which is targeted by the second expression modulating compound is ubiquitin, preferably ubiquitin B. Ubiquitin is a small protein that occurs in all eukaryotic cells. It performs a myriad of functions through conjugation to a large range of target proteins. A variety of different modifications can occur. The ubiquitin protein is highly conserved among eukaryotic species. A protein is marked with ubiquitin (ubiquitylation or ubiquitination) by a series of steps. Following addition of a single ubiquitin moiety to a protein substrate (monoubiquitination), further ubiquitin molecules can be added to the first, yielding a polyubiquitin chain. The ubiquitination system functions in a wide variety of central cellular processes, including apoptosis, cell cycle and division, DNA transcription and repair and differentiation and development.

Thus, both target genes, encoding Plk1 and ubiquitin are involved in central processes of the cell. As is shown in the examples, the use of a combination of expression modulating compounds such as RNAi mediating compounds (siRNAs) targeting the Plk1 and the ubiquitin mRNA results in a very efficient silencing effect and thus induces apoptosis in a large variety of cells. The induced phenotype (apoptosis) is clearly visibly detectable which allows the assessment of the transfection efficiency already within 48 hours after transfection. Apoptosis was induced in several different human cell lines, such as Huh 7, 293 and HepG2 cells and also in other cells such as e.g. mouse and rat cells.

According to a further embodiment, the expression modulating compound is directed against a non-coding RNA element. According to one embodiment, short interspersed nuclear elements (SINEs) are targeted by the expression modulating compound. SINEs are short DNA sequences (usually less than 500 bases) that are often repeated and are positioned relatively freely throughout the genome. SINEs can make up about 13% of the human genome. SINEs usually do not encode a functional reverse transcriptase protein and rely on other mobile elements for transposition. The most common SINEs in primates are called Alu sequences or Alu elements. According to the present knowledge, Alu elements are usually approximately 280 or 300 base pairs long, do not contain coding sequences, and can be recognized by the restriction enzyme AluI. The short interspersed nuclear (SINE) Alu elements in humans and the analogous B1 and B2 elements in mice have succeeded in becoming the most abundant mobile elements within the genomes, comprising ~10% of the human and ~6% of the mouse genome, respectively. Alu-sequences are often duplicated internally, which means that they comprise a 5' section and a 3' section which are related to each other, usually they are homologous. Usually, the Alu sequences are flanked by two short sequences (usually 7 to 20 bp), so-called direct repeats. These elements are often found in the untranslated region(s) of protein-expressing transcripts, usually in the 3' UTR. By targeting these repetitive elements, several genes are silenced, thereby inducing/promoting apoptosis in the cell.

According to one embodiment, a combination of expression modulating compounds targeting ubiquitin, preferably ubiquitin B and a SINE element, preferably a B1 repetitive element is used as a positive control. As is shown in the examples, the respective combination also induces apoptosis in a large variety of cells.

According to one embodiment, at least two of the following target sequences are targeted by the combination of expression modulating compounds:

```
                                    (SEQ. ID No. 1)
a.      Plk1-1:         CCGGATCAAGAAGAATGAATA (SEQ. ID No. 2)
b.      Plk1-2:         CGCGGGCAAGATTGTGCCTAA (SEQ. ID No. 3)
c.      Ubiquitin B1:   AAGGCCAAGATCCAAGATAAA
```

According to the standard applied in the prior art, the target sequence is indicated/shown as the corresponding DNA sequence. The expression modulating compound, and in particular the RNAi mediating compound can be designed based upon said sequence using conventional methods to recognize said target sequence and to efficiently induce silencing, preferably via RNAi. As is outlined above, in case the RNAi mediating compound is a siRNA compound, it may comprise ribose—as well as desoxyribose nucleotides or modified nucleotides.

According to one embodiment, the combination comprises an expression modulating compound that targets a B1 repetitive element. The target sequence of a B1 repetitive element may be selected from the group consisting of

```
B1_1:   CAGGCGGATTTCTGAGTTCGA   (SEQ. ID No. 4)

B1_2:   AGCCAGGGCTACACAGAGAAA   (SEQ. ID No. 5)

B1_3:   CAGAGGCAGGCGGATTTCTGA   (SEQ. ID No. 6)

B1_4:   CATGGTGGCGCACGCCTTTAA   (SEQ. ID No. 7)
```

A correspondingly designed RNAi mediating compound against a respective B1 repetitive element and in particular a siRNA targeting the respective B1 repetitive element is in particular specific for mouse and rat cells. As is shown in the examples, a siRNA against a respective target sequence is very effective in inducing apoptosis in mouse and rat cells. Furthermore, also expression modulating compounds targeting different combinations of the above mentioned target sequences can be used in conjunction with the present invention.

According to a further embodiment, a combination of an expression modulating compound targeting a repetitive element as described above and an expression modulating compound targeting the expression of a gene involved in apoptosis and thus a central metabolic process of the cell is used as a positive control in an expression modulating assay. This has the particular advantage that the effectivity of the positive control can be enhanced, e.g. by reducing the time necessary for achieving a visible apoptotic phenotype.

A gene involved in a central metabolic process is in particular a gene that is relevant for the proper maintenance of the cell viability and thus e.g. a gene involved in the cell cycle, apoptosis, cell division, DNA transcription, replication and repair or cell differentiation and development. Silencing of a respective gene induces, respectively promotes apoptosis. A suitable example for a respective gene is the ubiquitin gene or the plk1 gene.

The target sequence for ubiquitin may be selected from the group consisting of

```
Ubb_cs1   AAGGCCAAGATCCAGGATAAA   (SEQ. ID No. 8)

Ubb_cs2   AAGTTTAGAAATTACAAGTTT   (SEQ. ID No. 9)

Ubb_cs3   CGGCAAGACCATCACCCTGGA   (SEQ. ID No. 10)

Ubb_cs4   CGTGAAGACCCTGACCGGCAA   (SEQ. ID No. 11)
```

A correspondingly designed RNAi mediating compound against ubiquitin B and in particular a siRNA targeting the respective ubiquitin B target sequence silences the expression of ubiquitin B in human, mouse and rat cells as it matches the human, mouse and rat gene.

Furthermore, the target sequence may be selected from the group consisting of

```
Ubb_hs1:   CCTGTTCAAAATGTTAATAAA   (SEQ. ID No. 12)

Ubb_hs2:   AAGGCCAAGATCCAAGATAAA   (SEQ. ID No. 13)
```

-continued

```
Ubb_hs3:   CAGGATCCTGGTATCCGCTAA    (SEQ. ID No. 14)

Ubb_hs4:   CCAACTTAAGTTTAGAAATTA    (SEQ. ID No. 15)
```

A correspondingly designed RNAi mediating compound against human ubiquitin and in particular a siRNA targeting the respective human ubiquitin target sequence silences the expression of ubiquitin B in human cells. Thus, correspondingly designed RNAi mediating compounds show a specificity for human cells.

The target sequence for Oki may be selected from the group consisting of

```
cs_plk1-857:
CAGTATTCCCAAGCACATCAA           (SEQ. ID No. 16)

cs_plk1-1604:
CCGCAGCGCCATCATCCTGCA           (SEQ. ID No. 17)

cs_plk1-174:
CCGGAGGTCCTAGTGGACCCA           (SEQ. ID No. 18)

cs_plk1-1403:
CCTGCAGTACATAGAGCGTGA           (SEQ. ID No. 19)
```

A correspondingly designed RNAi mediating compound against plk1 and in particular a siRNA targeting the respective plk1 target sequence silences the expression of plk1 in human, mouse and rat cells as it matches the human, mouse and rat gene.

Furthermore, the target sequence for plk1 may be selected from the group consisting of

```
plk1-2083:  CACCATATGAATTGTACAGAA (SEQ. ID No. 20)

plk1-935:   AACCATTAACGAGCTGCTTAA (SEQ. ID No. 21)

plk1-2151:  TAAACAGATGTGAATATTCAA (SEQ. ID No. 22)

plk1-1473:  AAGAAGATCACCCTCCTTAAA (SEQ. ID No. 23)

plk1-542:   CTGCCAGTACCTGCACCGAAA (SEQ. ID No. 24)

plk1-2146:  CACATTAAACAGATGTGAATA (SEQ. ID No. 25)

plk1-278:   CAAGGAGGTGTTCGCGGGCAA (SEQ. ID No. 26)

plk1-1631:  CAACGGCAGCGTGCAGATCAA (SEQ. ID No. 27)

plk1-1637:  CAGCGTGCAGATCAACTTCTT (SEQ. ID No. 28)
```

A correspondently designed RNAi mediating compound against the human plk1 gene, and in particular a siRNA targeting the respective plk1 target sequence, silences the expression of plk1 in human cells.

Appropriate RNAi mediating compounds such as siRNAs which bind the corresponding mRNA transcript can be designed according to methods which are well-known and also well established. Targeting of the respective transcripts by the RNAi inducing compounds results in efficient gene silencing.

For convenience purposes it is preferred that a mixture of the first and second expression modulating compound targeting the expression of different genes, such as Plk1 and ubiquitin or ubiquitin and a B1 repetitive element is used for transfection, as this decreases the number of necessary individual steps for transfection which makes it more convenient for the user.

The first and the second expression modulating compound can be species-specific or may show cross-species specificity. The use of expression modulating compounds showing a cross-species specificity and which accordingly silence e.g. the expression of the corresponding genes in e.g. rat, mouse and/or human cells has the advantage that the positive control can be used for a variety of cells. However, the first and the second expression modulating compound can be specific for at least one cell species, selected from the group consisting of primate cells such as human cells and rodent cells such as rat cells and mouse cells.

According to one embodiment, the first and the second expression modulating compounds are specific for human cells. This allows the use of said compounds as human cell specific controls, e.g. in xenographic models.

According to one embodiment, the combination according to the present invention can be efficiently used for transfection in a concentration selected from the group consisting of at least 5 nM, at least 10 nM, at least 25 nM and at least 50 nM.

Many compounds may be used in order to regulate the expression of the first and sec- and target genes involved in apoptosis on a post-transcriptional level. Examples of appropriate expression modulators include but are not limited to small organic molecules, nucleic acids, peptides, cyclic peptides, antisense molecules, RNAi mediating compounds, and ribozymes. Respective modulators are well-known to the skilled person and were also outlined above. Please refer to our above comments for details.

According to one embodiment, the expression modulating compound is a RNAi inducing compound, preferably an siRNA. Examples of RNAi mediating compounds include but are not limited to short interfering nucleic acids (siNA), short interfering RNA (siRNA), microRNA (miRNA) and short hairpin RNAs (shRNA) as well as precursors thereof which are processed in the cell to the actual RNAi mediating compound. Preferably, said compound is a siRNA. As siRNA, said compound is a double-stranded molecule preferably having 3' overhangs on each strand. Said siRNA compound may comprise desoxy—as well as ribonucleotides and furthermore, modified nucleotides. Several embodiments and variations of siRNA compounds are known and can be used in conjunction with the present invention. The length of said siRNA is usually between 18 and 35 nt, preferably between 19 and 27 nt. The 3' overhangs on each end if present are preferably 2 nts long. In order to efficiently induce silencing, the siRNA used as RNAi inducing compound is substantially complementary to a portion of the target gene transcript for inhibiting the expression of said target transcript by RNA interference. Suitable siRNAs targeting the chosen/identified target sequences of the target genes on the RNA level can be identified by using proper computational methods, applying certain design-algorithms. Several methods are known and can be used in conjunction with the present invention in order to provide siRNAs efficiently silencing the expression of the first and second gene involved in apoptosis, which are preferably ubiquitin and plk-1.

In order to obtain a siRNA of the above structure against the target transcript, the double-stranded molecule can be transfected directly into the cell. Alternatively, this structure may result by processing by dicer, an enzyme that converts either long dsRNAs or small hairpin RNAs (shRNAs) into siRNAs (see above). These precursors or the final siRNA molecules can be produced exogenously (artificially) and can then be introduced into the cells to be analyzed by various transfection methods, to analyze the specific knockdown of the target genes involved in apoptosis.

According to a further embodiment, the expression modulating and in particular the RNAi inducing compound inhibiting the expression of the first and second target gene involved in apoptosis is expressed by a vector. This embodiment is advantageous, as e.g. transfection of an exogenous siRNA or antisense molecule can be sometimes problematic, since the gene knockdown effect is only transient, particularly in rapidly dividing cells. One way of overcoming this challenge is to modify the expression modulating compound such as a siRNA in such a way as to allow it to be expressed by an appropriate vector, for example a plasmid. For siRNA, this done by the introduction of a loop between the two strands, thus producing a single transcript, which can be then processed into a functional siRNA in the cell. Such transcription cassettes typically use an RNA polymerase 3 promoter (for example U6 or H1) which usually direct the transcription of small nuclear RNAs (shRNAs) (U6 is involved in gene's placing; H1 is the RNA subcomponent of human RNAse p). It is assumed that the resulting shRNA transcript from the vector is then processed by dicer, thereby producing the double-stranded siRNA molecules, preferably having the characteristic 3' overhangs.

According to one embodiment, a combination of
a) a RNAi inducing compound targeting the transcript of the ubiquitin gene and
b) a RNAi inducing compound targeting the transcript of the Plk1 gene
is used as positive control in an RNAi assay.

According to a further embodiment, a combination of
a) a RNAi inducing compound targeting the transcript of a ubiquitin gene, preferably ubiquitin B and
b) a RNAi inducing compound targeting the transcript of at least one SINE element, preferably an Alu or B1 repetitive element;
is used as positive control in an RNAi assay.

As is outlined above, these repetitive elements are often found in the untranslated regions of protein-coding transcripts. Targeting of these elements thus silences several genes, thereby disturbing the cell function and leading to apoptosis. Suitable target sequences are described above.

According to a preferred embodiment, the following target sequences are targeted by the combination of at least two expression modulating compounds:

```
Ubb_cs4    CGTGAAGACCCTGACCGGCAA    (SEQ. ID No. 11)

B1_4:      CATGGTGGCGCACGCCTTTAA   (SEQ. ID No. 7)
```

Ubb_cs4 (Cs_ubb_4) matches to mouse, rat and human ubiquitin B. The siRNA targeting the respective B1 repetitive elements is specific for mouse and rat cells. As is shown in the examples, a combination of siRNAs directed against the respective target sequences is very effective in inducing apoptosis. Furthermore, also expression modulating compounds targeting different combinations of the above mentioned target sequences can be used in conjunction with the present invention.

Furthermore, a method for performing an expression modulating analysis or assay is provided, wherein an apoptosis inducing combination of at least
a) a first expression modulating compound silencing the expression of a first target gene involved in apoptosis and
b) a second expression modulating compound silencing the expression of second target gene involved in apoptosis
is introduced into cells to induce apoptosis in the cells. The combination of expression modulating compounds according to the invention can be used as a positive control which is detectable based on the phenotype of the cells, as the combination induces apoptosis in the cells.

As is outlined above, using at least two different expression modulating compounds targeting different genes involved in apoptosis is advantageous, as an easy to detect phenotype is induced in the cells as a result of the gene silencing. Of course, any method can be used that allows detection of apoptosis, but visual analysis is preferred.

Further embodiments/features of this method, the expression modulating compounds and suitable target sequences were already outlined above in conjunction with the description of the use of respective expression modulating compounds as positive controls. These features/embodiments equally apply to the provided method according to the present invention. This in particular pertains to the defined examples of expression modulating compounds and the embodiment, wherein the effect of said expression modulating compound such as an RNAi inducing compound on the expression of the target genes involved in apoptosis is analyzed by microscopy technologies.

According to one preferred embodiment, the first expression modulating compound is an RNAi inducing compound (preferably an siRNA), which is substantially complementary to at least a portion of the plk-1 mRNA and the second expression modulating compound is an RNAi inducing compound (preferably an siRNA), which is substantially complementary to at least a portion of the ubiquitin mRNA for inhibiting the expression of said target mRNAs by RNA interference thereby inducing apoptosis in the trans-fected cells.

As is also outlined above, the RNAi inducing compound can be a siRNA. The siRNA is preferably substantially complementary to a portion of the respective target gene transcript for inhibiting the expression of said target transcript by RNA interference. Suitable examples of respective siRNAs and ways to generate them are described above and equally apply to the provided method.

Also provided is an expression modulation analysis kit, comprising
a first expression modulating compound silencing the expression of a first target gene involved in apoptosis and
a second expression modulating compound silencing the expression of a second target gene involved in apoptosis as positive control. The kit may comprise optionally buffers and transfection reagents.

As outlined above, silencing is preferably achieved via the RNAi pathway. Suitable examples and embodiments are described in detail above and also apply in conjunction with the kit according to the present invention.

The kit may comprise further components, such as other expression modulating compounds such as e.g. siRNAs for knockdown of the desired target genes, negative controls, reagents, such as for example transfection reagents and/or buffers.

A respective kit allows the rapid detection of the transfection efficiency. As outlined above, the phenotype induced by the combination according to the present invention (targeting two different target genes involved in apoptosis), the apoptotic phenotype can be detected in less than 72 hours. Preferably, said phenotype is detectable in less than 60 hours and even less than 50 hours as it is achieved when targeting the Plk1 and ubiquitin gene. The specific characteristics of the expression modulating compounds are described above.

Further details regarding said positive control are described in detail above; we refer to the above disclosure.

As is outlined above, phenotypic controls are particularly suitable for high through put assays, wherein several experiments are performed in parallel using a substrate comprising several reaction spots, such as for example a microtiter plate (having multiple wells) or a transfection chip (comprising multiple hydrophilic spots surrounded by hydrophobic areas). The expression modulating compounds that are used for the HTS experiments are often ordered by the customer at the manufacturer who then provides the compounds, e.g. siRNA in the reaction spots of the substrate in the desired arrangement. Hence, the positive control according to the present invention can be provided in the reaction spots of the substrate, such as for example in the wells of a microtiter plate or on the hydrophilic spots of a transfection chip. The customer then only needs to add the cells and proper media for cell growth and start the analysis. Thereby, a convenient system for the user is provided.

Therefore, the invention also provides a substrate comprising multiple reaction spots suitable for performing transfection reactions (for example a microtiter plate comprising wells or a wall-less setting on a transfection chip comprising multiple hydrophilic reaction spots surrounded by hydrophobic areas), wherein at least one of the reaction spot comprises a combination of a first expression modulating compound silencing the expression of a first target gene involved in apoptosis and a second expression modulating compound silencing the expression of a second target gene involved in apoptosis as positive control.

Therefore, the positive control according to the present invention may already be provided in/on the substrate and can therefore be easily incorporated in the experiments. Optionally, the substrate may also comprise further expression modulating compounds used in the actual experiments, such as for example customized RNAi inducing compounds, such as siRNAs.

According to one embodiment, the substrate comprises wells or hydrophilic spots on a substantially flat surface which are surrounded by hydrophobic areas.

Also provided is an RNAi inducing composition/combination inducing apoptosis in cells comprising at least two of the following a) an RNAi inducing compound targeting the transcript of the ubiquitin gene and b) an RNAi inducing compound targeting the transcript of the Plk1 gene;

c) an RNAi inducing compound targeting the transcript of at least one SINE element, preferably an Alu or B1 repetitive element. As is outlined above, these repetitive elements are often found in the untranslated regions of protein-coding transcripts.

A respective combination can be advantageously used as a control to monitor transfection efficiency. The respective composition preferably targets a transcript comprising a sequence derived from at least one of the following target sequences:

```
Plk1-1:      CCGGATCAAGAAGAATGAATA (SEQ ID NO: 1)

Plk1-2:      CGCGGGCAAGATTGTGCCTAA (SEQ ID NO: 2)

Ubiquitin B1: AAGGCCAAGATCCAAGATAAA (SEQ ID NO: 3)
```

Further suitable species specific and cross-species specific target sequences are described in detail above, we refer to the above disclosure.

According to a preferred embodiment the composition targets a transcript comprising a sequence derived from at least one of the following target sequences

```
Cs_ubb_4:    CGTGAAGACCCTGACCGGCAA  (SEQ ID NO: 11)

B1_4:        CATGGTGGCGCACGCCTTTAA. (SEQ ID NO: 7).
```

A respective composition can be used in RNAi experiments as described above in order to monitor the transfection efficiency. The combination/composition according to the present invention which is based on the use of two different expression modulating compounds silencing the expression of two different target genes may, however, also be used in in vivo experiments (besides in vitro and ex vivo transfection assays).

For example, the first and second expression modulating compound silencing different target genes involved in apoptosis (preferably silencing the plk-1 and the ubiquitin gene) can be administered to tumor bearing mice and thus mice, where human tumor cells were implanted. Administration of the first and second compound may occur simultaneously or consecutively. By giving human specific RNAi inducing compounds such as siRNAs in vivo to the human tumor cell carrying mice, this leads to an elimination of the tumor without attacking the mouse cells and thus the endogenous mouse cells. For these applications, the RNAi inducing compounds are preferably human specific.

Accordingly, the combination of the present invention can also be used e.g. as delivery control in xenographic tumor models, in which human tumor cells are grown in animal models. The toxic expression modulating compounds of the present invention would only target the implanted human cells but would not affect the mice cells/tissue. This provides a novel, valuable delivery control for gene silencing experiments in xenographic animal models of human diseases.

Furthermore, the combination of the present invention may also be used in therapy and in particular in order to attack tumor cells. By using RNAi inducing compounds as described above, which silence the expression of genes involved in apoptosis and which particularly targets the plk and the ubiquitin gene transcript, a targeted elimination of tumor cells from the organism to be treated is possible.

The invention thus also pertains to a pharmaceutical composition comprising a composition as described above. A respective composition may also be used for the manufacture of a medicament for the treatment of tumor cells. Also a combination treatment, wherein the first and second expression modulating compounds according to the present invention are administered consecutively is within the scope of the present invention.

The present invention is now described by way of non-limiting examples.

FIG. 1 Discloses the effects of a Plk1 specific siRNA on different cells. In accordance with previous publications, the transfection with a Plk1 specific siRNA results 48 hours and 72 hours after transfection in visible cytotoxic effects in MCF-7 and HeLaS3 cells which are determinable by a normal microscope. FIG. 1 shows as a way of example a typical experiment 48 hours after transfection.

FIG. 2 The down regulation of Plk1 does not induce a detectable apoptosis in other human cell lines such as 293, A549, CaCo, HeLa, HepG2 or Huh7 even when the analysis was performed 4 days after transfection. Basically no detectable phenotype (apoptosis) was seen. FIG. 2 shows as an example typical pictures taken from the microscope of 293 cells 2 days after transfection.

FIGS. 3A-3G show the results of an experiment using an ubiquitin B specific siRNA. After two or three days signs of cell death are visible. However, the effects are 48 hours after the transfection not as prominent in order to allow determination of the transfection efficiently and safely. As can be seen, different cell lines using different siRNA concentrations were tested.

FIG. 4 The ubiquitin B siRNA used in the experiments and shown in FIG. 3 is specific for human cells. Transfection of the mouse cell line NIH/3T3 which the siRNA did not have any influence on the detectable cell death. The results are shown in FIG. 4.

FIG. 5 Shows that by combining the ubiquitin B siRNA and the Plk1 specific siRNA results in a prominent phenotype which is easily detectable when using simple equipment such as a microscope. This enables the assessment of the transfection already 48 hours or even 45 hours after transfection. This safes time. Also included is a comparison with a toxic siRNA, which is commercially available (Dharmacon siRNA). As the example shows, the apoptotic phenotype is easy to detect with the teaching of the present invention.

FIG. 6 Shows the results of fast forward transfection assays with siRNAs targeting the expression of ubiquitin B and B1 repetitive elements. The target sequences were

```
Ubb_cs4    CGTGAAGACCCTGACCGGCAA    (SEQ. ID No. 11)
B1_4:      CATGGTGGCGCACGCCTTTAA    (SEQ. ID No. 7)
```

$2 \times 10^4$ cells were used per well. 50, 25 or 10 nM siRNA were mixed with 3 ul (microliter) of a transfection reagent, here a cationic lipid. The transfection complexes were used with 100 ul and 500 ul cell suspension. The results show that the mixture of cross-species specific ubiquitin (ubb4) and a B1 repetitive target sequence (B1-4) works very efficiently at 10 nM. In FIG. 6, NIH3T3 cells were used. Here, the results obtained 48 h after transfection are shown.

SEQUENCE LISTING

<160> NUMBER OF SEQ ID NOS: 28

Figure 1:
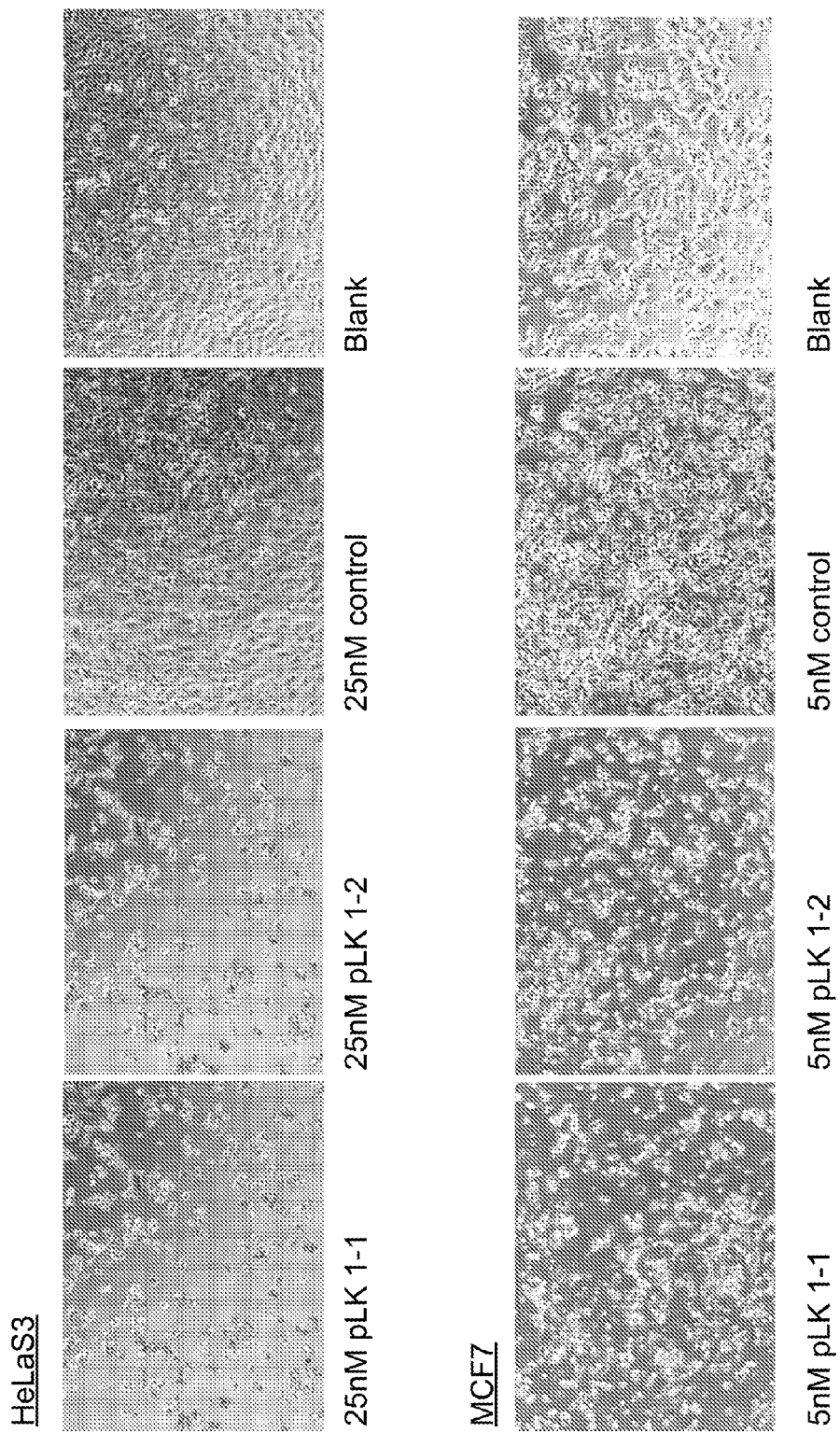
Figure 2:
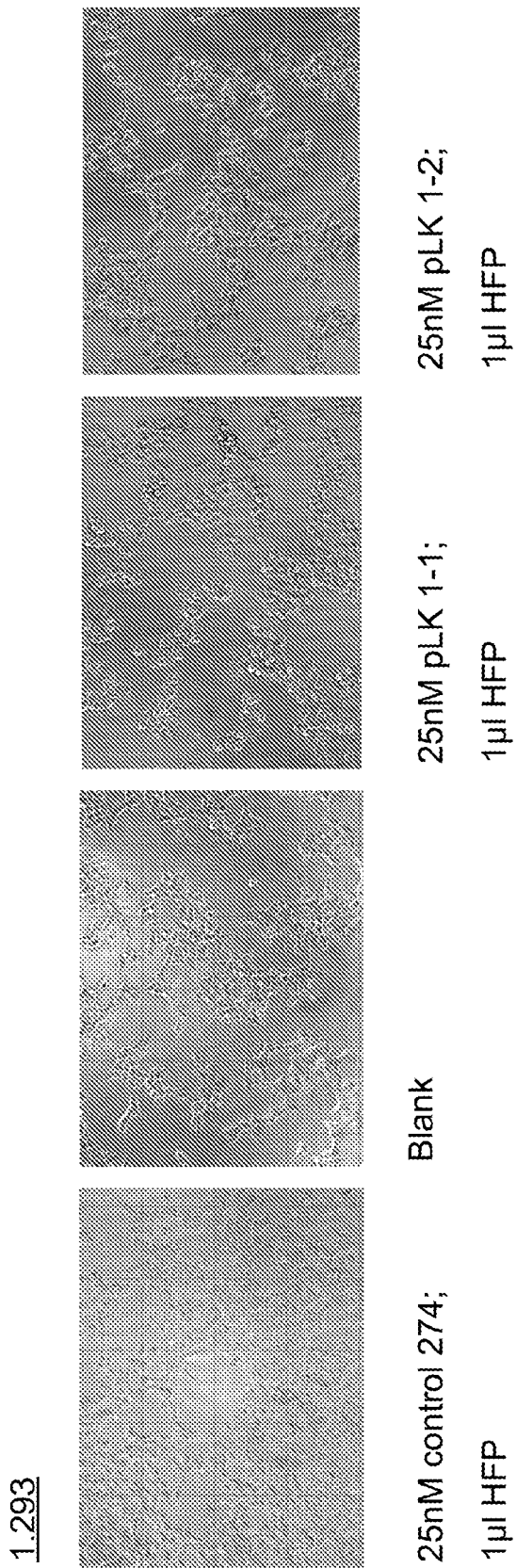
Figure 3B:
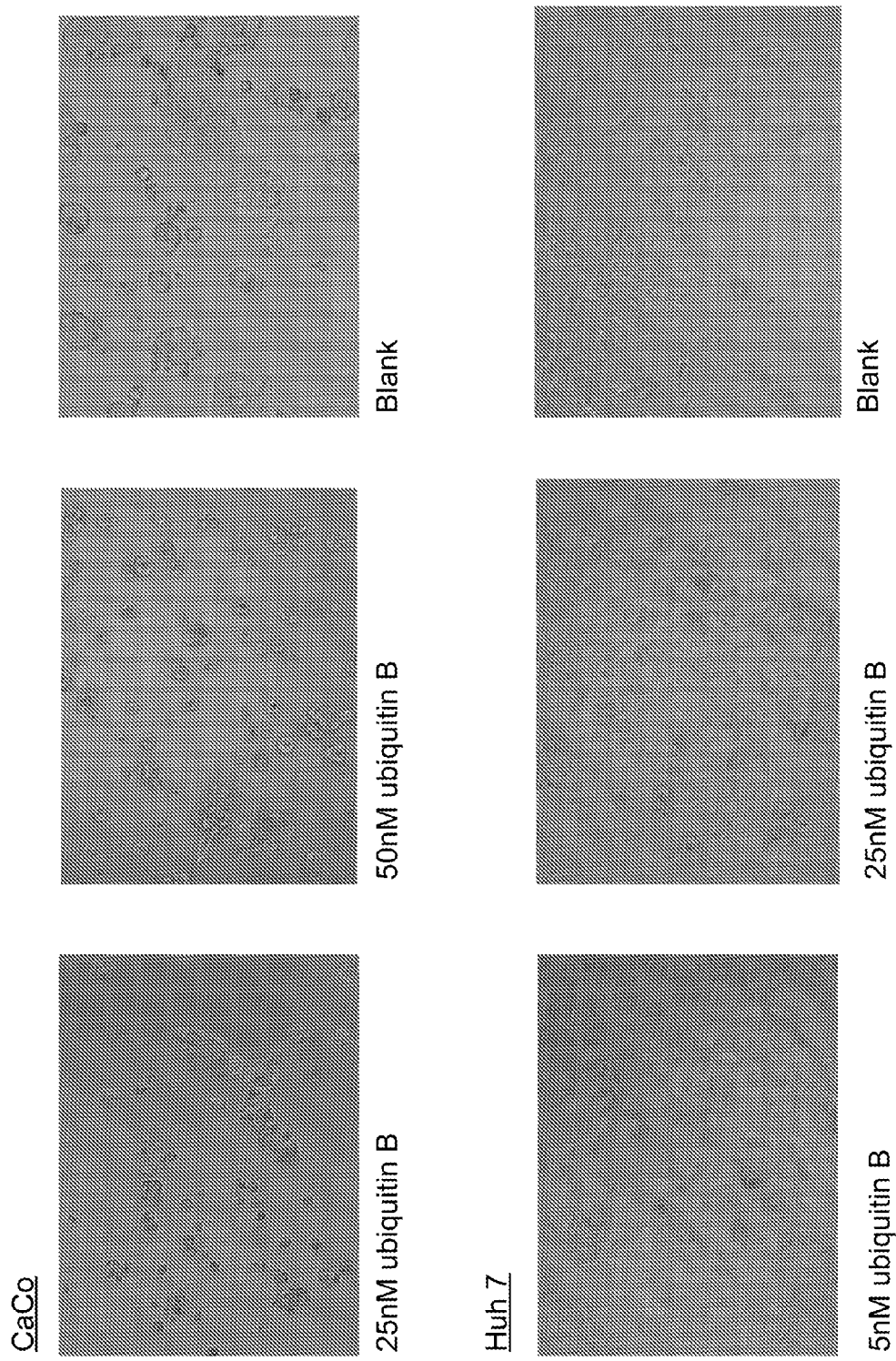
Figure 3C:
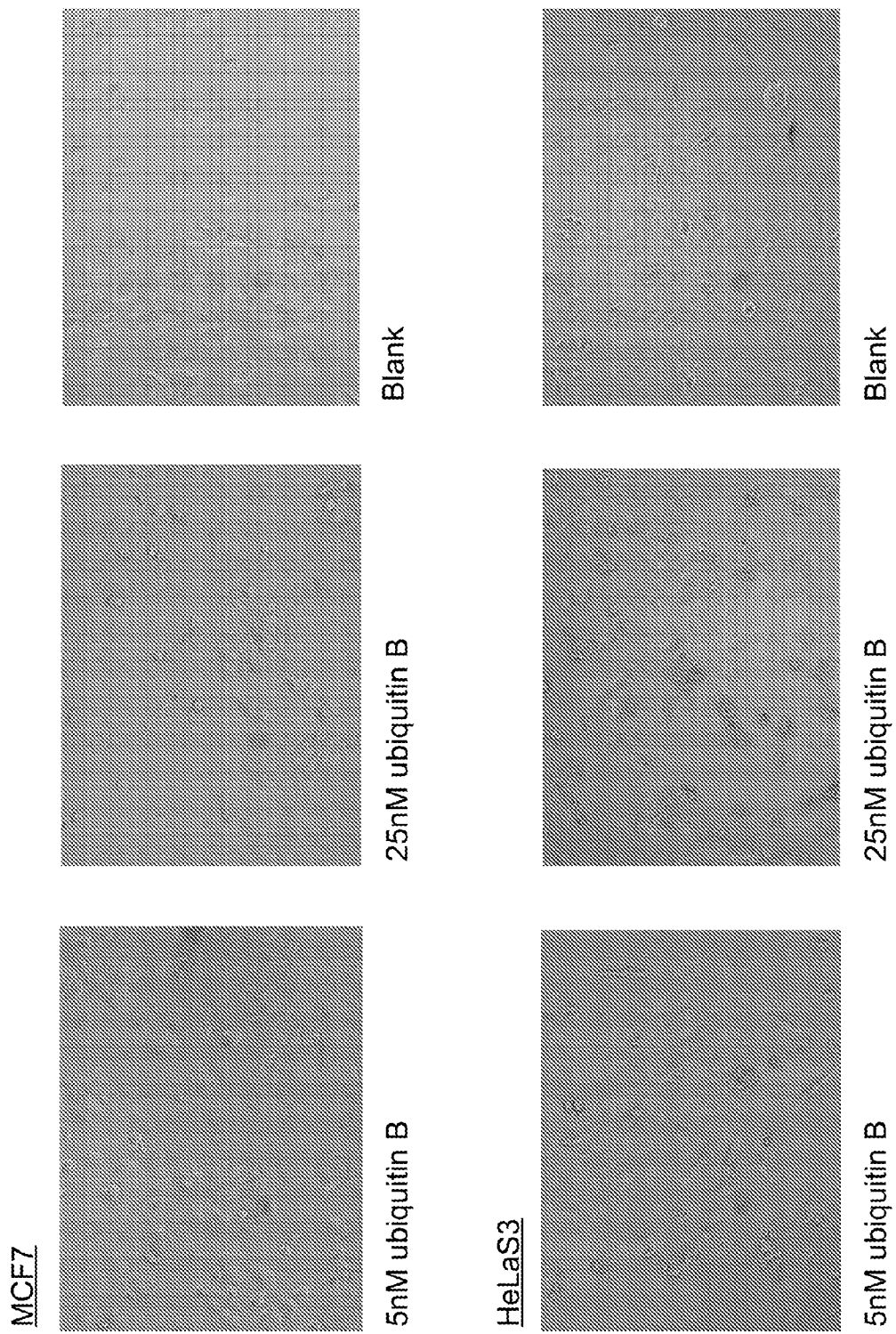
Figure 3E:
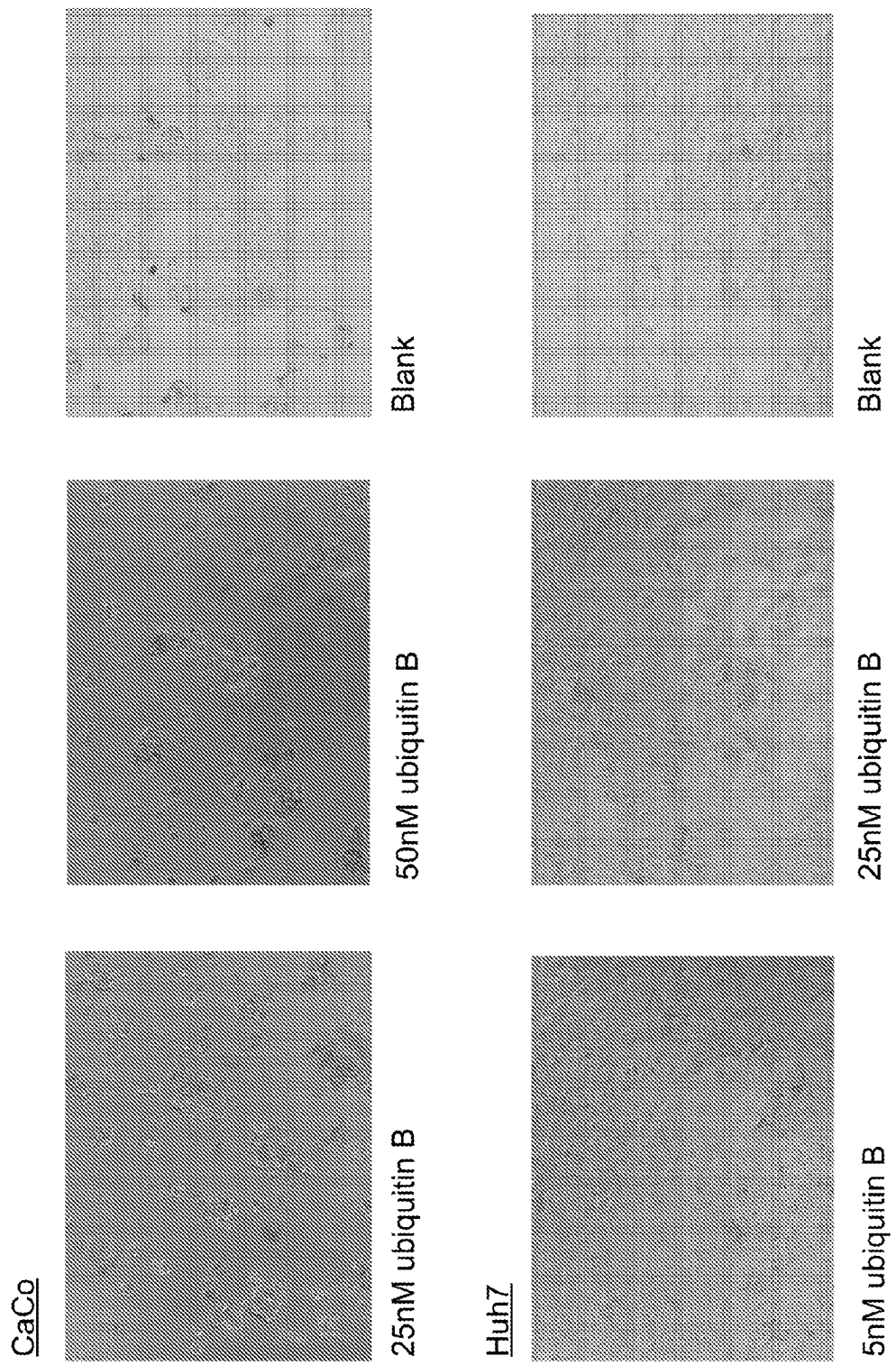
Figure 4:
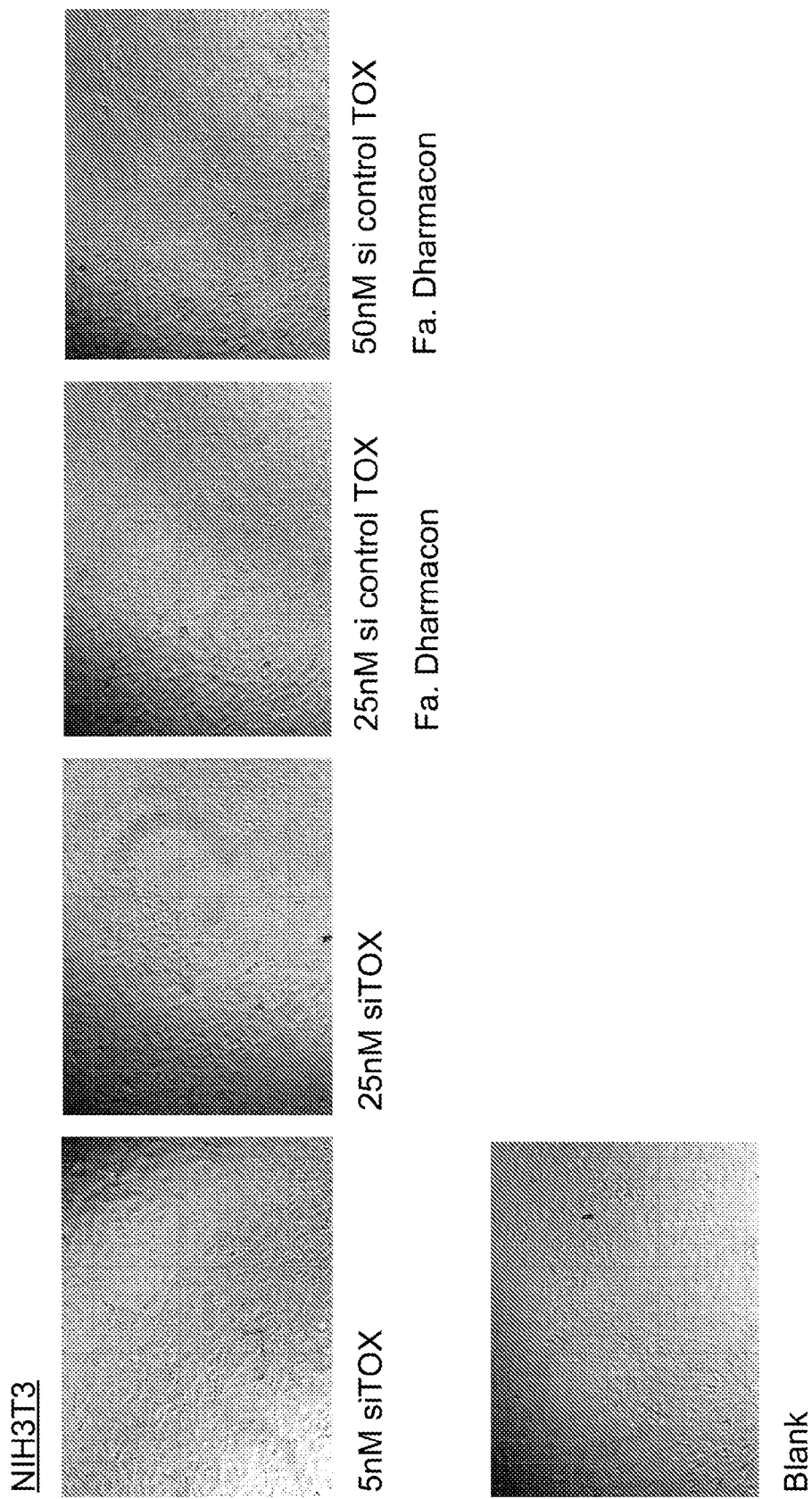
Figure 5:
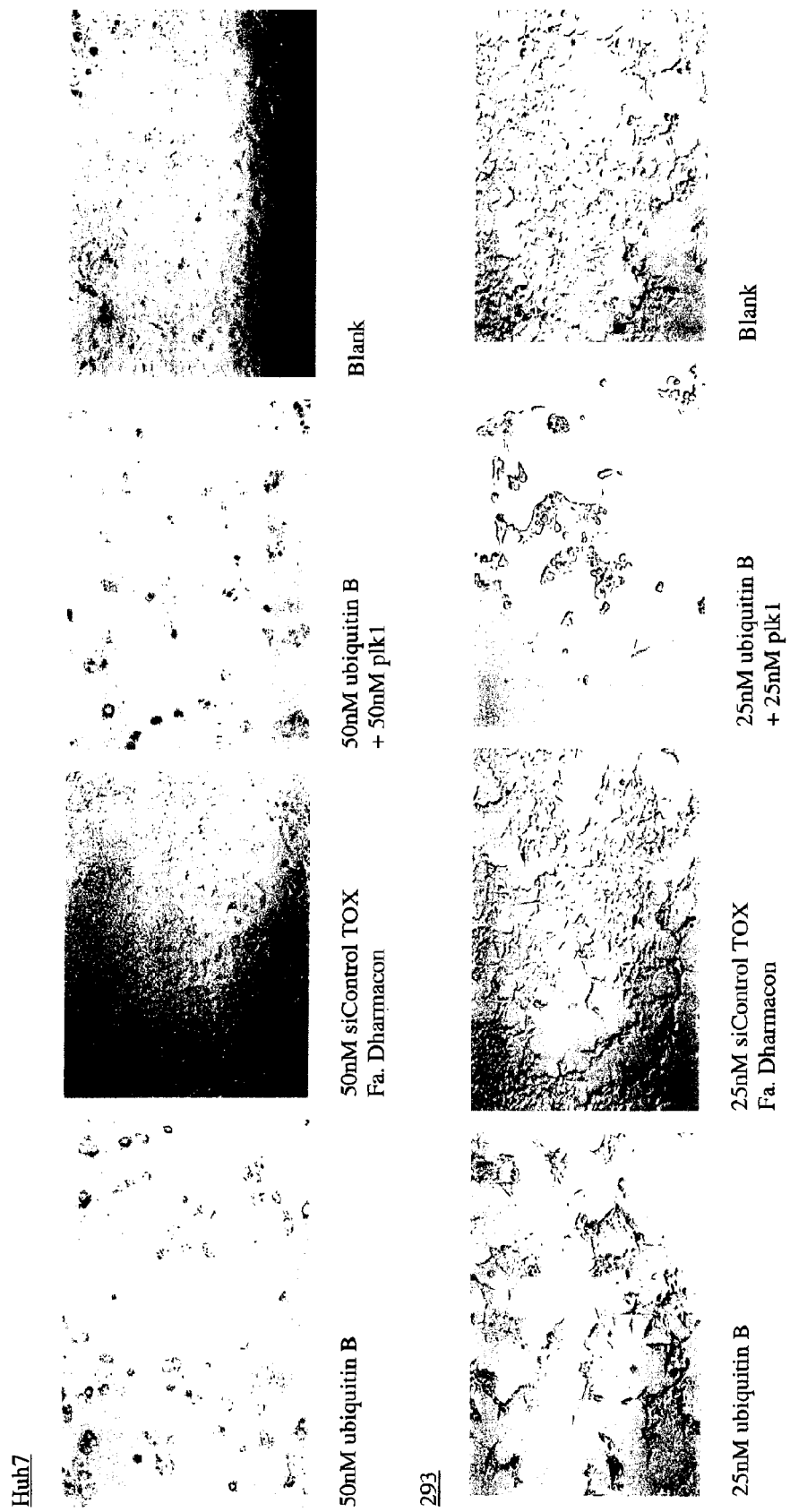
Figure 6:
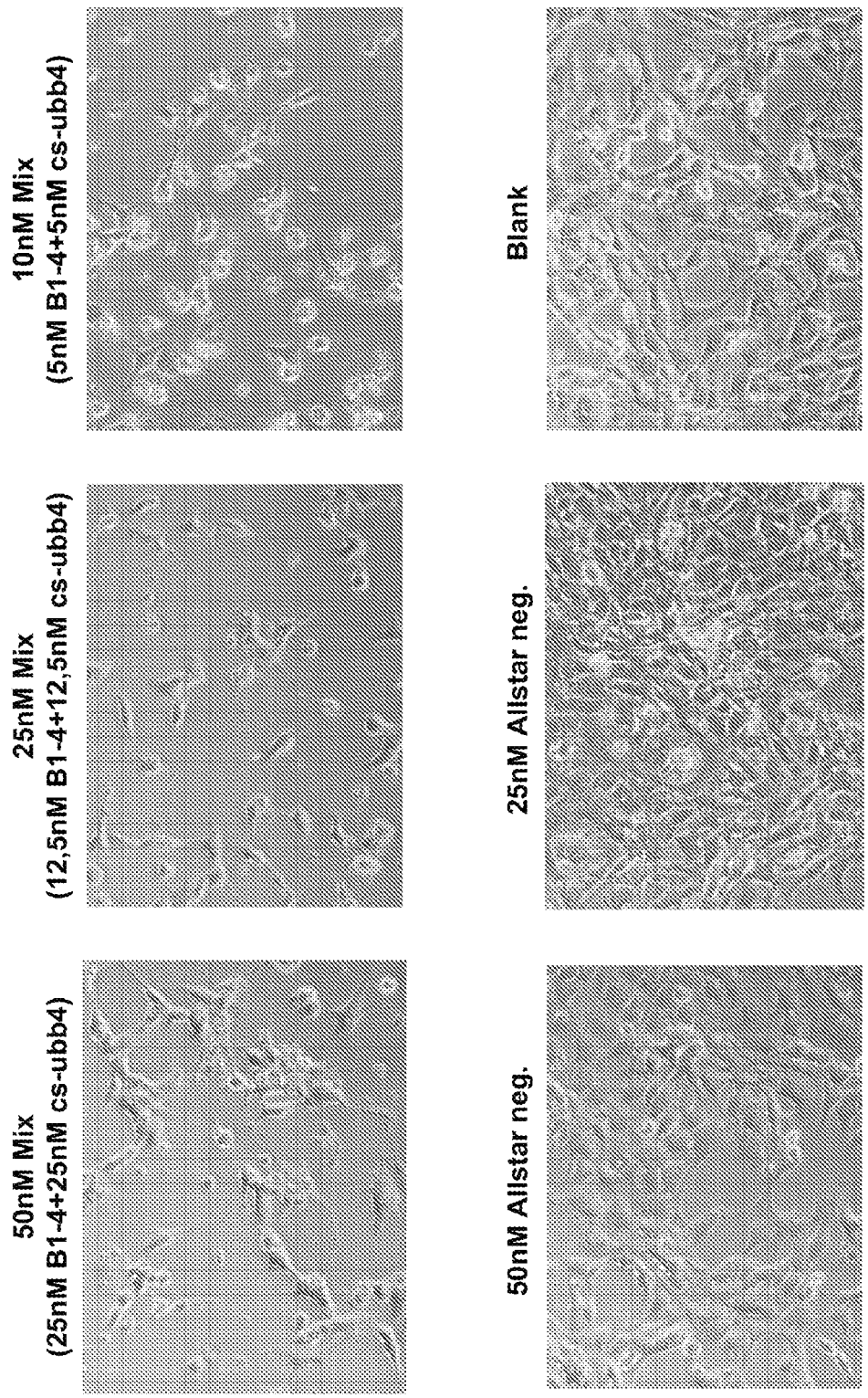
Figure 7:
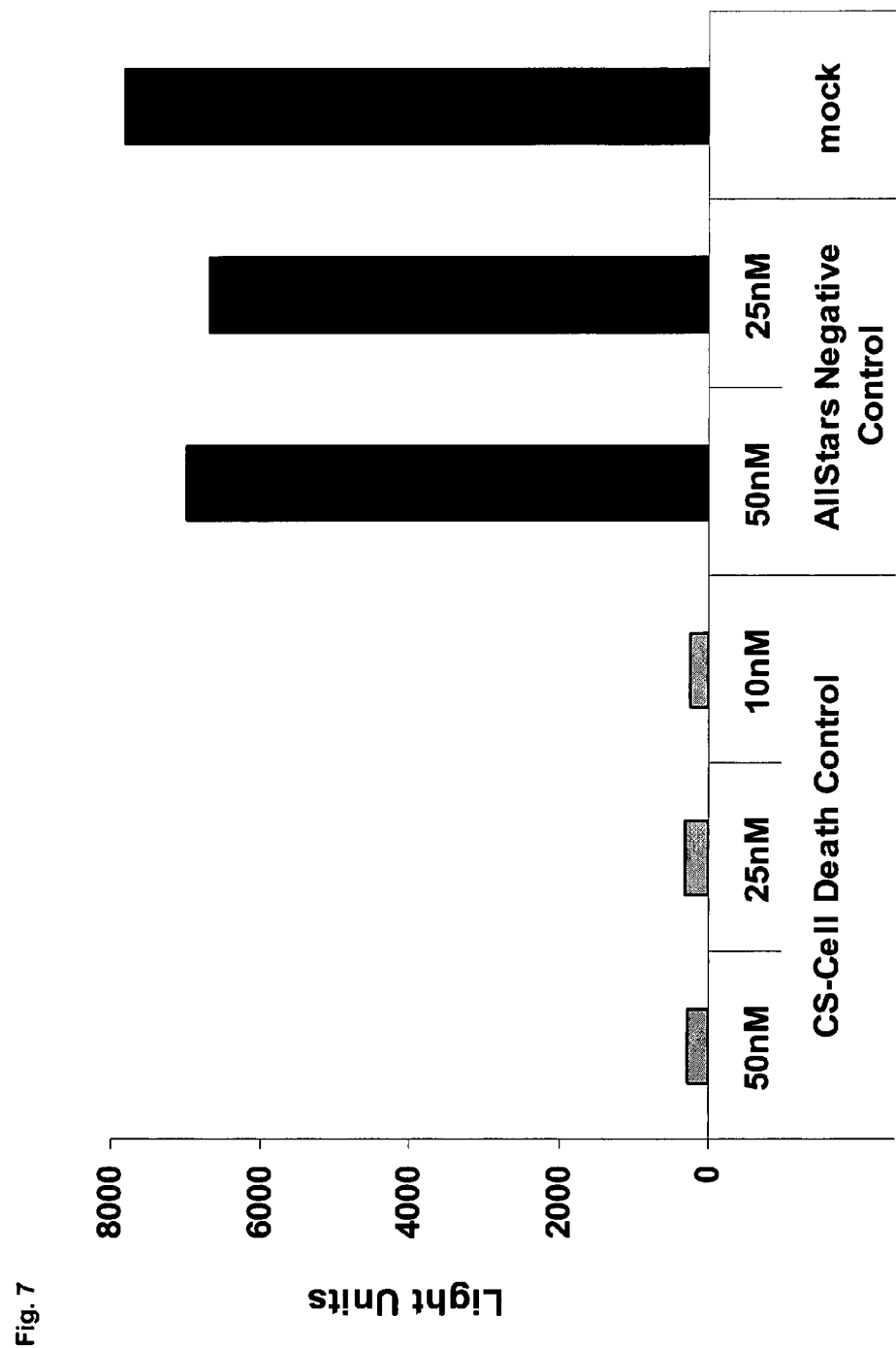
FIG. 7 Shows the results of a quantification of cell numbers using CellTiter Glo Assay (Promega) (mock=blank). The results shows significant induction of cell death upon transfection with the siRNA mixture that was also used in the experiment shown in FIG. 6 (CS-cell death control).
Figure 8:
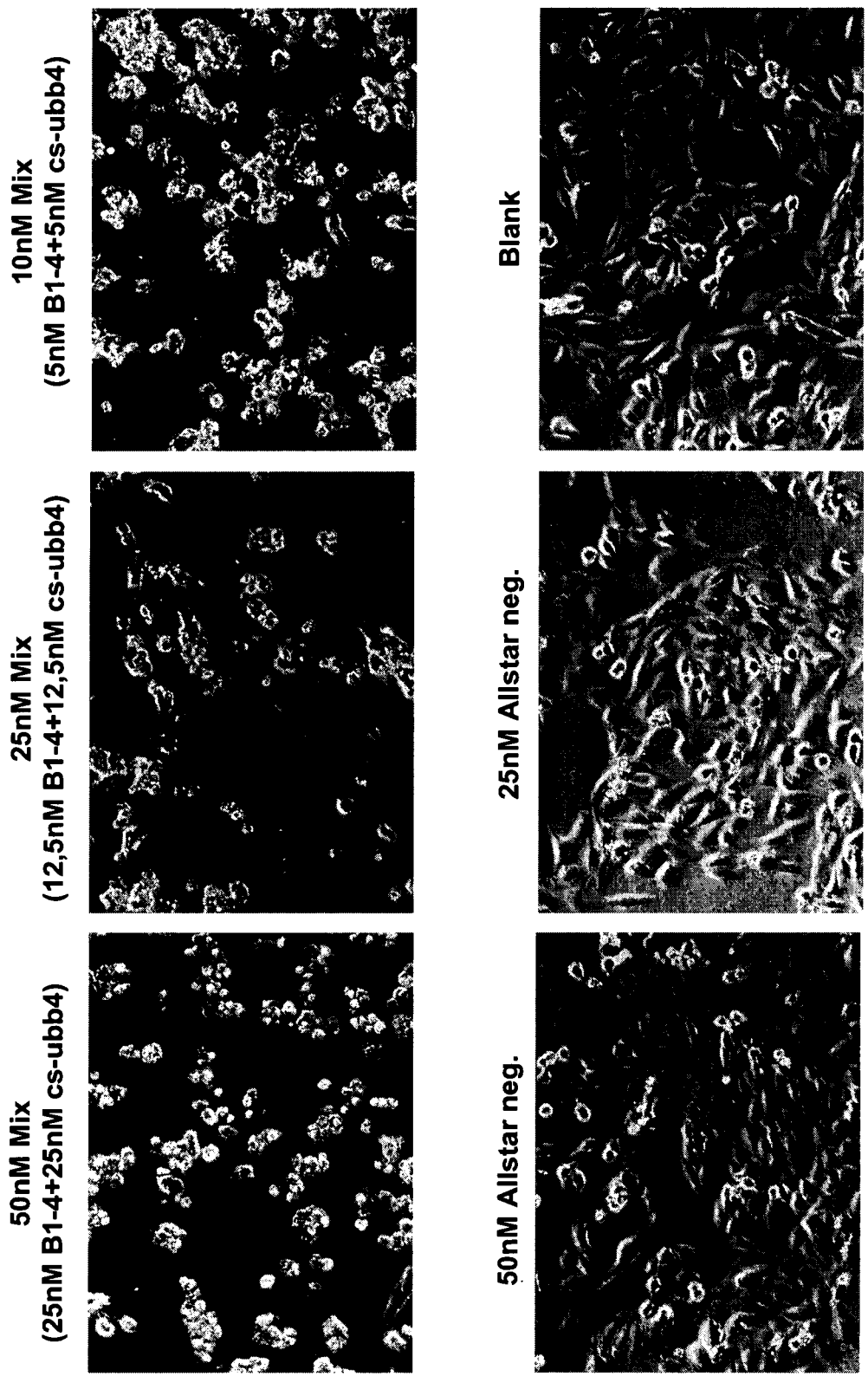
FIG. 8 Shows the results obtained with L6 cells upon transfection with the siRNA mixture that was also used in the experiment shown in FIG. 6. Here, the results obtained 48 h after transfection are shown.

<210> SEQ ID NO 1
<211> LENGTH: 21
<212> TYPE: DNA
<213> ORGANISM: Artificial Sequence
<220> FEATURE:
<223> OTHER INFORMATION: Target sequence of Plk1 (Plk1-1)

<400> SEQUENCE: 1
ccggatcaag aagaatgaat a                                        21

<210> SEQ ID NO 2
<211> LENGTH: 21
<212> TYPE: DNA
<213> ORGANISM: Artificial Sequence
<220> FEATURE:
<223> OTHER INFORMATION: Target sequence of Plk1 (Plk1-2)

<400> SEQUENCE: 2
cgcgggcaag attgtgccta a                                        21

<210> SEQ ID NO 3
<211> LENGTH: 21
<212> TYPE: DNA
<213> ORGANISM: Artificial Sequence
<220> FEATURE:
<223> OTHER INFORMATION: Target sequence ubiquitin B1

<400> SEQUENCE: 3
aaggccaaga tccaagataa a                                        21

<210> SEQ ID NO 4
<211> LENGTH: 21
<212> TYPE: DNA
<213> ORGANISM: Artificial Sequence
<220> FEATURE:
<223> OTHER INFORMATION: Target sequence of a B1 repetitive element
       specific for mouse and rat

<400> SEQUENCE: 4
caggcggatt tctgagttcg a                                        21

-continued

<210> SEQ ID NO 5
<211> LENGTH: 21
<212> TYPE: DNA
<213> ORGANISM: Artificial Sequence
<220> FEATURE:
<223> OTHER INFORMATION: Target sequence of a B1 repetitive element
      specific for mouse and rat

<400> SEQUENCE: 5
agccagggct acacagagaa a                                              21

<210> SEQ ID NO 6
<211> LENGTH: 21
<212> TYPE: DNA
<213> ORGANISM: Artificial Sequence
<220> FEATURE:
<223> OTHER INFORMATION: Target sequence of a B1 repetitive element
      specific for mouse and rat

<400> SEQUENCE: 6
cagaggcagg cggatttctg a                                              21

<210> SEQ ID NO 7
<211> LENGTH: 21
<212> TYPE: DNA
<213> ORGANISM: Artificial Sequence
<220> FEATURE:
<223> OTHER INFORMATION: Target sequence of a B1 repetitive element
      specific for mouse and rat

<400> SEQUENCE: 7
catggtggcg cacgccttta a                                              21

<210> SEQ ID NO 8
<211> LENGTH: 21
<212> TYPE: DNA
<213> ORGANISM: Artificial Sequence
<220> FEATURE:
<223> OTHER INFORMATION: Target sequence of Ubiquitin B specific for
      human, mouse and rat

<400> SEQUENCE: 8
aaggccaaga tccaggataa a                                              21

<210> SEQ ID NO 9
<211> LENGTH: 21
<212> TYPE: DNA
<213> ORGANISM: Artificial Sequence
<220> FEATURE:
<223> OTHER INFORMATION: Target sequence of Ubiquitin B specific for
      human, mouse and rat

<400> SEQUENCE: 9
aagtttagaa attacaagtt t                                              21

<210> SEQ ID NO 10
<211> LENGTH: 21
<212> TYPE: DNA
<213> ORGANISM: Artificial Sequence
<220> FEATURE:
<223> OTHER INFORMATION: Target sequence of Ubiquitin B specific for
      human, mouse and rat

<400> SEQUENCE: 10
cggcaagacc atcaccctgg a                                              21

<210> SEQ ID NO 11

```
<211> LENGTH: 21
<212> TYPE: DNA
<213> ORGANISM: Artificial Sequence
<220> FEATURE:
<223> OTHER INFORMATION: Target sequence of Ubiquitin B specific for
      human, mouse and rat

<400> SEQUENCE: 11
cgtgaagacc ctgaccggca a                                              21

<210> SEQ ID NO 12
<211> LENGTH: 21
<212> TYPE: DNA
<213> ORGANISM: Artificial Sequence
<220> FEATURE:
<223> OTHER INFORMATION: Target sequence of Ubiquitin specific for
      human Ubiquitin

<400> SEQUENCE: 12
cctgttcaaa atgttaataa a                                              21

<210> SEQ ID NO 13
<211> LENGTH: 21
<212> TYPE: DNA
<213> ORGANISM: Artificial Sequence
<220> FEATURE:
<223> OTHER INFORMATION: Target sequence of Ubiquitin specific for
      human Ubiquitin

<400> SEQUENCE: 13
aaggccaaga tccaagataa a                                              21

<210> SEQ ID NO 14
<211> LENGTH: 21
<212> TYPE: DNA
<213> ORGANISM: Artificial Sequence
<220> FEATURE:
<223> OTHER INFORMATION: Target sequence of Ubiquitin specific for
      human Ubiquitin

<400> SEQUENCE: 14
caggatcctg gtatccgcta a                                              21

<210> SEQ ID NO 15
<211> LENGTH: 21
<212> TYPE: DNA
<213> ORGANISM: Artificial Sequence
<220> FEATURE:
<223> OTHER INFORMATION: Target sequence of Ubiquitin specific for
      human Ubiquitin

<400> SEQUENCE: 15
ccaacttaag tttagaaatt a                                              21

<210> SEQ ID NO 16
<211> LENGTH: 21
<212> TYPE: DNA
<213> ORGANISM: Artificial Sequence
<220> FEATURE:
<223> OTHER INFORMATION: Target sequence of plk1 specific for
      human, mouse and rat

<400> SEQUENCE: 16
cagtattccc aagcacatca a                                              21

<210> SEQ ID NO 17
<211> LENGTH: 21
<212> TYPE: DNA
```

```
<213> ORGANISM: Artificial Sequence
<220> FEATURE:
<223> OTHER INFORMATION: Target sequence of plk1 specific for
      human, mouse and rat

<400> SEQUENCE: 17
ccgcagcgcc atcatcctgc a                                              21

<210> SEQ ID NO 18
<211> LENGTH: 21
<212> TYPE: DNA
<213> ORGANISM: Artificial Sequence
<220> FEATURE:
<223> OTHER INFORMATION: Target sequence of plk1 specific for
      human, mouse and rat

<400> SEQUENCE: 18
ccggaggtcc tagtggaccc a                                              21

<210> SEQ ID NO 19
<211> LENGTH: 21
<212> TYPE: DNA
<213> ORGANISM: Artificial Sequence
<220> FEATURE:
<223> OTHER INFORMATION: Target sequence of plk1 specific for
      human, mouse and rat

<400> SEQUENCE: 19
cctgcagtac atagagcgtg a                                              21

<210> SEQ ID NO 20
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 20
caccatatga attgtacaga a                                              21

<210> SEQ ID NO 21
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 21
aaccattaac gagctgctta a                                              21

<210> SEQ ID NO 22
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 22
taaacagatg tgaatattca a                                              21

<210> SEQ ID NO 23
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 23
```

```
aagaagatca ccctccttaa a                                             21

<210> SEQ ID NO 24
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 24
ctgccagtac ctgcaccgaa a                                             21

<210> SEQ ID NO 25
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 25
cacattaaac agatgtgaat a                                             21

<210> SEQ ID NO 26
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 26
caaggaggtg ttcgcgggca a                                             21

<210> SEQ ID NO 27
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 27
caacggcagc gtgcagatca a                                             21

<210> SEQ ID NO 28
<211> LENGTH: 21
<212> TYPE: DNA
<213> ORGANISM: Artificial Sequence
<220> FEATURE:
<223> OTHER INFORMATION: Target sequence of plk1 specific for human plk1

<400> SEQUENCE: 28
cagcgtgcag atcaacttct t                                             21
```

The invention claimed is:

1. A method for performing an expression-modulating assay, comprising:

transfecting a cell with an apoptosis-inducing combination of at least a) a first expression-modulating compound silencing the expression of at least a first target gene involved in apoptosis, wherein said first target gene is Plk1, and b) a second expression-modulating compound silencing the expression of at least a second target gene involved in apoptosis, wherein said second target gene is ubiquitin, thereby performing an expression-modulating assay, wherein the apoptosis-inducing combination is used as a positive control in the expression-modulating assay, and wherein the expression-modulating assay is for analyzing gene-silencing effects.

2. The method according to claim 1, wherein a) the apoptosis-inducing combination induces a visible apoptotic phenotype in the cell transfected with the apoptosis-inducing combination in less than 72 hours;

b) the second target gene is ubiquitin B;

c) the apoptosis-inducing combination also targets a repetitive element;

d) the apoptosis-inducing combination targets at least one of the following target sequences and silences the expression of at least one of the corresponding genes:

```
                              (SEQ. ID No. 1)
Plk1-1:          CCGGATCAAGAAGAATGAATA, (SEQ. ID No. 2)
Plk1-2:          CGCGGGCAAGATTGTGCCTAA,
and (SEQ. ID No. 3)
Ubiquitin B1:    AAGGCCAAGATCCAAGATAAA;
``` e) the apoptosis-inducing combination targets at least one of the following target sequences and silences the expression of at least one of the corresponding genes:

```
                              (SEQ. ID No. 4)
B1_1:            CAGGCGGATTTCTGAGTTCGA, (SEQ. ID No. 5)
B1_2:            AGCCAGGGCTACACAGAGAAA, (SEQ. ID No. 6)
B1_3:            CAGAGGCAGGCGGATTTCTGA, (SEQ. ID No. 7)
B1_4:            CATGGTGGCGCACGCCTTTAA, (SEQ. ID No. 8)
Ubb_cs1          AAGGCCAAGATCCAGGATAAA, (SEQ. ID No. 9)
Ubb_cs2          AAGTTTAGAAATTACAAGTTT, (SEQ. ID No. 10)
Ubb_cs3          CGGCAAGACCATCACCCTGGA, (SEQ. ID No. 11)
Ubb_cs4          CGTGAAGACCCTGACCGGCAA, (SEQ. ID No. 12)
Ubb_hs1:         CCTGTTCAAAATGTTAATAAA, (SEQ. ID No. 13)
Ubb_hs2:         AAGGCCAAGATCCAAGATAAA, (SEQ. ID No. 14)
Ubb_hs3:         CAGGATCCTGGTATCCGCTAA, (SEQ. ID No. 15)
Ubb_hs4:         CCAACTTAAGTTTAGAAATTA, (SEQ. ID No. 16)
cs_plk1-857:     CAGTATTCCCAAGCACATCAA, (SEQ. ID No. 17)
cs_plk1-1604:    CCGCAGCGCCATCATCCTGCA, (SEQ. ID No. 18)
cs_plk1-174:     CCGGAGGTCCTAGTGGACCCA, (SEQ. ID No. 19)
cs_plk1-1403:    CCTGCAGTACATAGAGCGTGA, (SEQ. ID No. 20)
plk1-2083:       CACCATATGAATTGTACAGAA, (SEQ. ID No. 21)
plk1-935:        AACCATTAACGAGCTGCTTAA, (SEQ. ID No. 22)
plk1-2151:       TAAACAGATGTGAATATTCAA, (SEQ. ID No. 23)
plk1-1473:       AAGAAGATCACCCTCCTTAAA,
```

```
                              (SEQ. ID No. 24)
plk1-542:        CTGCCAGTACCTGCACCGAAA, (SEQ. ID No. 25)
plk1-2146:       CACATTAAACAGATGTGAATA, (SEQ. ID No. 26)
plk1-278:        CAAGGAGGTGTTCGCGGGCAA, (SEQ. ID No. 27)
plk1-1631:       CAACGGCAGCGTGCAGATCAA,
and (SEQ. ID No. 28)
plk1-1637:       CAGCGTGCAGATCAACTTCTT;
``` f) the apoptosis-inducing combination targets at least one of the following target sequences and silences the expression of at least one of the corresponding genes:

```
Ubb_cs4:
CGTGAAGACCCTGACCGGCAA,       (SEQ. ID No. 11)
and

B1_4:
CATGGTGGCGCACGCCTTTAA;       (SEQ. ID No. 7)
``` g) the first and second expression-modulating compounds are specific for human cells; or h) the first and second expression-modulating compounds are specific for at least one cell species selected from the group consisting of human cells, rat cells and mouse cells.

3. The method according to claim 1, wherein the combination is used for transfection at a concentration selected from the group consisting of at least 5 nM, at least 10 nM, at least 25 nM and at least 50 nM.

4. The method according to claim 1, wherein
a) the first or second expression-modulating compound is an RNAi-inducing compound;
b) the first or second expression-modulating compound is an siRNA, an miRNA or an shRNA and silences the expression of the target genes via RNAi;
c) the first or second expression-modulating compound is an siRNA double-stranded molecule of 18 to 30 nucleotides; or
d) the first or second expression-modulating compound is expressed by a vector.

5. A method for performing an expression-modulating analysis or assay, comprising:
introducing into cells an apoptosis-inducing combination of at least
a) a first expression-modulating compound silencing the expression of at least a first target gene involved in apoptosis, wherein the first target gene is Plk1, and
b) a second expression-modulating compound silencing the expression of at least a second target gene involved in apoptosis, wherein said second target gene is ubiquitin,
to induce apoptosis in the cells.

6. The method according to claim 5, wherein
a) the first and the second expression-modulating compounds are introduced in form of a composition;
b) the introduced first and second expression-modulating compounds together induce a visible apoptotic phenotype in the cells having the first and second expression-modulating compounds introduced in less than 72 hours; or
c) the first and second expression-modulating compounds are introduced in form of a composition at a concentration selected from the group consisting of at least 5 nM, at least 10 nM, at least 25 nM and at least 50 nM.

7. The method according to claim 5, wherein the first expression-modulating compound is an RNAi-inducing compound that is substantially complementary to at least a portion of the mRNA of the first target gene for inhibiting the expression of said first target gene by RNA interference, and the second expression-modulating compound is an RNAi-inducing compound that is substantially complementary to at least a portion of the mRNA of the second target gene for inhibiting the expression of said second target gene by RNA interference.

8. The method according to claim 5, wherein:

a) the apoptosis-inducing combination induces a visible apoptotic phenotype in the cells having the apoptosis-inducing combination introduced in less than 72 hours;

b) the apoptosis-inducing combination targets at least one of the following target sequences and silences the expression of at least one of the corresponding genes:

```
Plk1-1:
CCGGATCAAGAAGAATGAATA,        (SEQ. ID No. 1)

Plk1-2:
CGCGGGCAAGATTGTGCCTAA,        (SEQ. ID No. 2)
and

Ubiquitin B1:
AAGGCCAAGATCCAAGATAAA;        (SEQ. ID No. 3)
``` c) the apoptosis-inducing combination targets at least one of the following target sequences and silences the expression of at least one of the corresponding genes:

```
B1_1:
CAGGCGGATTTCTGAGTTCGA,        (SEQ. ID No. 4)

B1_2:
AGCCAGGGCTACACAGAGAAA,        (SEQ. ID No. 5)

B1_3:
CAGAGGCAGGCGGATTTCTGA,        (SEQ. ID No. 6)

B1_4:
CATGGTGGCGCACGCCTTTAA,        (SEQ. ID No. 7)

Ubb_cs1
AAGGCCAAGATCCAGGATAAA,        (SEQ. ID No. 8)

Ubb_cs2
AAGTTTAGAAATTACAAGTTT,        (SEQ. ID No. 9)

Ubb_cs3
CGGCAAGACCATCACCCTGGA,        (SEQ. ID No. 10)

Ubb_cs4
CGTGAAGACCCTGACCGGCAA,        (SEQ. ID No. 11)

Ubb_hs1:
CCTGTTCAAAATGTTAATAAA,        (SEQ. ID No. 12)

Ubb_hs2:
AAGGCCAAGATCCAAGATAAA,        (SEQ. ID No. 13)

Ubb_hs3:
CAGGATCCTGGTATCCGCTAA,        (SEQ. ID No. 14)

Ubb_hs4:
CCAACTTAAGTTTAGAAATTA,        (SEQ. ID No. 15)

cs_plk1-857:
CAGTATTCCCAAGCACATCAA,        (SEQ. ID No. 16)

cs_plk1-1604:
CCGCAGCGCCATCATCCTGCA,        (SEQ. ID No. 17)

cs_plk1-174:
CCGGAGGTCCTAGTGGACCCA,        (SEQ. ID No. 18)

cs_plk1-1403:
CCTGCAGTACATAGAGCGTGA,        (SEQ. ID No. 19)

plk1-2083:
CACCATATGAATTGTACAGAA,        (SEQ. ID No. 20)

plk1-935:
AACCATTAACGAGCTGCTTAA,        (SEQ. ID No. 21)

plk1-2151:
TAAACAGATGTGAATATTCAA,        (SEQ. ID No. 22)

plk1-1473:
AAGAAGATCACCCTCCTTAAA,        (SEQ. ID No. 23)

plk1-542:
CTGCCAGTACCTGCACCGAAA,        (SEQ. ID No. 24)

plk1-2146:
CACATTAAACAGATGTGAATA,        (SEQ. ID No. 25)

plk1-278:
CAAGGAGGTGTTCGCGGGCAA,        (SEQ. ID No. 26)

plk1-1631:
CAACGGCAGCGTGCAGATCAA,        (SEQ. ID No. 27)
and plk1-1637:
CAGCGTGCAGATCAACTTCTT;        (SEQ. ID No. 28)
``` d) the apoptosis-inducing combination targets at least one of the following target sequences and silences the expression of at least one of the corresponding genes:

```
Ubb_cs4:
CGTGAAGACCCTGACCGGCAA,        (SEQ. ID No. 11)
and

B1_4:
CATGGTGGCGCACGCCTTTAA;        (SEQ. ID No. 7)
``` e) the first and second expression-modulating compounds are specific for human cells;

f) the first and second expression-modulating compounds are specific for at least one cell species selected from the group consisting of human cells, rat cells and mouse cells;

g) the apoptosis-inducing combination is introduced at a concentration selected from the group consisting of at least 5 nM, at least 10 nM, at least 25 nM and at least 50 nM;

h) the first or second expression-modulating compound is an RNAi-inducing compound;

i) the first or second expression-modulating compound is an siRNA, an miRNA or an shRNA and silences the expression of the target genes via RNAi;

j) the first or second expression-modulating compound is an siRNA double-stranded molecule of 18 to 30 nucleotides;

k) the first or second expression-modulating compound is expressed by a vector; or l) the first and second expression-modulating compounds are:
  (i) an RNAi-inducing compound targeting the transcript of the Plk1 gene, and
  (ii) an RNAi-inducing compound targeting the transcript of the ubiquitin gene, respectively.

9. An RNAi inducing composition capable of inducing apoptosis comprising:
a) an RNAi-inducing compound targeting the transcript of a ubiquitin gene; and
b) an RNAi-inducing compound targeting the transcript of a Plk1 gene.

10. The composition according to claim 9, wherein
a) the composition targets at least one of the following target sequences and silences the expression of at least one of the corresponding genes:

```
Plk1-1:
CCGGATCAAGAAGAATGAATA,      (SEQ. ID No. 1)

Plk1-2:
CGCGGGCAAGATTGTGCCTAA,      (SEQ. ID No. 2)
and

Ubiquitin B1:
AAGGCCAAGATCCAAGATAAA;      (SEQ. ID No. 3)
``` b) the composition targets at least one of the following target sequences and silences the expression of at least one of the corresponding genes:

```
Ubb_cs4:
CGTGAAGACCCTGACCGGCAA,      (SEQ. ID No. 11)
and

B1_4:
CATGGTGGCGCACGCCTTTAA;      (SEQ. ID No. 7)
``` c) the composition induces a visible apoptotic phenotype in the transfected cells in less than 72 hours;
d) the composition targets the transcripts of the Plk1 gene and a Ubiquitin B gene;
e) the composition targets at least one of the following target sequences and silences the expression of at least one of the corresponding genes:

```
B1_1:
CAGGCGGATTTCTGAGTTCGA,      (SEQ. ID No. 4)

B1_2:
AGCCAGGGCTACACAGAGAAA,      (SEQ. ID No. 5)

B1_3:
CAGAGGCAGGCGGATTTCTGA,      (SEQ. ID No. 6)

B1_4:
CATGGTGGCGCACGCCTTTAA,      (SEQ. ID No. 7)

Ubb_cs1
AAGGCCAAGATCCAGGATAAA,      (SEQ. ID No. 8)

Ubb_cs2
AAGTTTAGAAATTACAAGTTT,      (SEQ. ID No. 9)

Ubb_cs3
CGGCAAGACCATCACCCTGGA,      (SEQ. ID No. 10)

Ubb_cs4
CGTGAAGACCCTGACCGGCAA,      (SEQ. ID No. 11)

Ubb_hs1:
CCTGTTCAAAATGTTAATAAA,      (SEQ. ID No. 12)

Ubb_hs2:
AAGGCCAAGATCCAAGATAAA,      (SEQ. ID No. 13)

Ubb_hs3:
CAGGATCCTGGTATCCGCTAA,      (SEQ. ID No. 14)

Ubb_hs4:
CCAACTTAAGTTTAGAAATTA,      (SEQ. ID No. 15)

cs_plk1-857:
CAGTATTCCCAAGCACATCAA,      (SEQ. ID No. 16)

cs_plk1-1604:
CCGCAGCGCCATCATCCTGCA,      (SEQ. ID No. 17)

cs_plk1-174:
CCGGAGGTCCTAGTGGACCCA,      (SEQ. ID No. 18)

cs_plk1-1403:
CCTGCAGTACATAGAGCGTGA,      (SEQ. ID No. 19)

plk1-2083:
CACCATATGAATTGTACAGAA,      (SEQ. ID No. 20)

plk1-935:
AACCATTAACGAGCTGCTTAA,      (SEQ. ID No. 21)

plk1-2151:
TAAACAGATGTGAATATTCAA,      (SEQ. ID No. 22)

plk1-1473:
AAGAAGATCACCCTCCTTAAA,      (SEQ. ID No. 23)

plk1-542:
CTGCCAGTACCTGCACCGAAA,      (SEQ. ID No. 24)

plk1-2146:
CACATTAAACAGATGTGAATA,      (SEQ. ID No. 25)

plk1-278:
CAAGGAGGTGTTCGCGGGCAA,      (SEQ. ID No. 26)

plk1-1631:
CAACGGCAGCGTGCAGATCAA,      (SEQ. ID No. 27)
and plk1-1637:
CAGCGTGCAGATCAACTTCTT;      (SEQ. ID No. 28)
``` f) the composition targets at least one of the following target sequences and silences the expression of at least one of the corresponding genes:

```
Ubb_cs4:
CGTGAAGACCCTGACCGGCAA,      (SEQ. ID No. 11)
and

B1_4:
CATGGTGGCGCACGCCTTTAA;      (SEQ. ID No. 7)
``` g) the RNA inducing compounds in the composition are specific for human cells;
h) the RNA inducing compounds in the composition are specific for at least one cell species selected from the group consisting of human cells, rat cells and mouse cells;
i) the composition is used for transfection at a concentration selected from the group consisting of at least 5 nM, at least 10 nM, at least 25 nM and at least 50 nM;
j) the RNAi-inducing compound is an siRNA, an miRNA or an shRNA;
k) the RNAi-inducing compound is an siRNA double-stranded molecule of 18 to 30 nucleotides; or
l) the first or second expression-modulating compound is expressed by a vector.

11. The composition according to claim 9, wherein the composition is on a reaction spot of a substrate comprising multiple reaction spots for performing a transfection reaction.

12. The method according to claim 5, wherein the expression-modulating analysis or assay is an RNAi experiment.

13. The composition of claim 9, wherein the composition is comprised in an expression-modulating kit.

14. The method according to claim 1, wherein the apoptosis-inducing combination is used as a positive control for transfection efficiency.

* * * * *